United States Patent [19]
Tsui et al.

[11] Patent Number: 6,063,913
[45] Date of Patent: May 16, 2000

[54] STABLE HETEROLOGOUS PROPAGATION CFTR PROTEIN VARIANT CDNA

[75] Inventors: Lap-Chee Tsui, Etobicoke; Johanna M. Rommens, Willowdale, both of Canada

[73] Assignee: HSC Research and Development Limited Partnership, Canada

[21] Appl. No.: 08/030,081

[22] PCT Filed: Sep. 20, 1991

[86] PCT No.: PCT/CA91/00341

§ 371 Date: Apr. 12, 1993

§ 102(e) Date: Apr. 12, 1993

[87] PCT Pub. No.: WO92/05252

PCT Pub. Date: Apr. 2, 1992

Related U.S. Application Data

[63] Continuation-in-part of application No. 07/401,609, Aug. 31, 1989, abandoned, which is a continuation of application No. 07/399,945, Aug. 24, 1989, abandoned, which is a continuation of application No. 07/396,894, Aug. 22, 1989, abandoned.

[30] Foreign Application Priority Data

Sep. 21, 1990 [GB] United Kingdom .................. 9020632

[51] Int. Cl.$^7$ ................................................ C07H 21/04
[52] U.S. Cl. .................. 536/23.5; 536/23.5; 435/320.1
[58] Field of Search ......................... 536/23.5; 435/320.1

[56] References Cited

U.S. PATENT DOCUMENTS

| | | | |
|---|---|---|---|
| 4,322,274 | 3/1982 | Wilson et al. | 204/180 G |
| 4,844,893 | 7/1989 | Honsik et al. | 424/85.8 |
| 4,847,201 | 7/1989 | Kaswasaki et al. | 435/70 |
| 4,853,331 | 8/1989 | Herrnstadt et al. | 435/252.1 |
| 4,861,589 | 8/1989 | Ju | 424/93 |
| 4,861,719 | 8/1989 | Miller | 435/236 |
| 4,868,116 | 9/1989 | Morgan et al. | 435/240.2 |
| 4,980,286 | 12/1990 | Morgan et al. | 435/172.3 |
| 5,240,846 | 8/1993 | Collins et al. | 435/240.1 |

FOREIGN PATENT DOCUMENTS

| | | |
|---|---|---|
| 0 226 288 | 6/1987 | European Pat. Off. . |
| 0 288 299 | 10/1988 | European Pat. Off. . |
| 0 446 017 | 9/1991 | European Pat. Off. . |
| 2 203 742 | 10/1988 | United Kingdom . |
| WO 91/02796 | 3/1991 | WIPO . |
| WO 91/10734 | 7/1991 | WIPO . |
| WO 92/05273 | 4/1992 | WIPO . |
| WO 93/17040 | 9/1993 | WIPO . |

OTHER PUBLICATIONS

"Correction of the Cystic Fibrosis Defect In Vitro by Retrovirus–Mediated Gene Transfer"; Drumm et al; pp. 1227–1233.

"Gamma–crystallins of the Human Eye Lens: Expression Analysis of Five Members of the Gene Family"; Meakin et al; pp. 2671–267.

"Lambda ZAP: a bacteriophage lambda expresion vector with in vivo excision properties"; Short et al; pp. 7583–7599.

"Identification of the Cystic Fibrosis Gene: Cloning and Characterization of Complementary DNA"; Riordan et al; pp. 1066–1073.

Bear et al., Purification and Functional Reconstitution of the Cystic Fibrosis Transmembrane Conductance Regulator (CFTR), *Cell* 68:809–818 (1992).

Rommens et al., cAMP–Inducible Chloride Conductance in Mouse Fibroblast Lines Stably Expressing the Human Cystic Fibrosis Transmembrane Conductance Regulator, *Proc. Natl. Acad. Sci. USA* 88:7500–7504 (1991).

Kartner et al., Expression of the Cystic Fibrosis Gene in Non–Epithelial Invertebrate Cells Produces a Regulated Anion Conductance, *Cell* 64:681–691 (1991).

Zielenski et al., Genomic DNA Sequence of the Cystic Fibrosis Transmembrane Conductance Regulator (CFTR) Gene, *Genomics* 10:214–228 (1991).

Drumm et al., Correction of the Cystic Fibrosis Defect in Vitro by Retrovirus–Mediated Gene Transfer, *Cell* 62:1227–1233 (1990).

Quinton, P.M., Cystic Fibrosis: A Disease in Electrolyte Transport, *FASEB J.* 4:2709–2717 (1990).

The Cystic Fibrosis Genetic Analysis Consortium, Worldwide Survey of the ΔF508 Mutation–Report from the Cystic Fibrosis Genetic Analysis Consortium, *Am J. Hum. Genet.* 47:354–359 (1990).

Venglarik et al., A Simple Assay for Agonist–Regulated Cl and K Conductances in Salt–Secreting Epithelial Cells, *Am. J. Physiol.* 259:C358–C364 (1990).

Kerem et al., Identification of Mutations in Regions Corresponding to the Two Putative Nucleotide (ATP)–Binding Folds of the Cystic Fibrosis Gene, *Proc. Natl. Acad. Sci. USA* 87:8447–8451 (1990).

Green et al., Chromosomal Region of the Cystic Fibrosis Gene in Yeast Artificial Chromosomes: A Model for Human Genome Mapping, *Science* 250:94–98 (1990).

Cliff et al., Separate Cl$^-$ Conductances Activated by cAMP and Ca$^{2+}$ in Cl$^-$–Secreting Epithelial Cells, *Proc. Natl. Acad. Sci. USA* 87:4956–4960 (1990).

Welsh, M.J. Abnormal Regulation of Ion Channels in Cystic Fibrosis Epithelia, *FASEB J.* 4:2718–2725 (1990).

Hyde et al., Structural Model of ATP–Binding Proteins Associated with Cystic Fibrosis, Multidrug Resistance and Bacterial Transport, *Nature* 346:362–365 (1990).

*Primary Examiner*—Stephanie W. Zitomer
*Attorney, Agent, or Firm*—Alston & Bird LLP

[57] ABSTRACT

A modified DNA sequence encoding full length cystic fibrosis transmembrane conductance regulator protein is provided to facilitate propagation and/or expression of the protein in living cells and in particular, bacterial cells. The modified DNA sequence comprises at least one of the 13 base pair repeat of exon 6b of the normal gene encoding the conductance regulator protein, as one or more normal nucleotides of the 13 base repeat substituted with an alternate nucleotide which, however, continues to code for the corresponding normal amino acid. Mammalian cells transfected with a vector containing the modified DNA sequence enhances chlorine conductance through the cell wall.

3 Claims, 31 Drawing Sheets

Cutting et al., A Cluster of Cystic Fibrosis Mutations in the First Nucleotide–Binding Fold of the Cystic Fibrosis Conductance Regulator Protein, *Nature 346*:366–369 (1990).

Slot et al., No Evidence for Expression of the Insulin–Regulatable Glucose Transporter in Endothelial Cells, *Nature 346*:369–371 (1990).

Dean et al., Multiple Mutations in Highly Conserved Residues are Found in Mildly Affected Cystic Fibrosis Patients, *Cell 61*:863–870 (1990).

Wilson, et al., Correction of CD18–Deficient Lymphocytes by Retrovirus–Mediated Gene Transfer, *Science 248*:1413–1416 (1990).

Schoumacher et al., A Cystic Fibrosis Pancreatic Adenocarcinom Cell Line, *Proc. Natl. Acad. Sci. USA 87:4012–4016 (1990)*.

White et al., A Frame–Shift Mutation in the Cystic Fibrosis Gene, *Nature 344*:665–667 (1990).

Wilson et al., Expression of Human Adenosine Deaminase in Mice Reconstituted with Retrovirus–Transduced Hamatopoietic Stem Cells, *Proc. Natl. Acad. Sci. USA 87*:439–443 (1990).

Boat et al., Cystic Fibrosis in The Metabolic Basis of Inherited Disease, vol. II, (Scriver et al., eds.) McGraw–Hill Information Services Company, N.Y., N.Y., pp. 2649–2679 (1989).

Sanbrook et al, Oligonucleotide–Mediated Mutagenesis in Molecular Cloning, A Laboratory Manual, 2nd Ed., Cold Spring Harbor Press, Cold Spring Harbor, NY, pp. 15.51–15.80 (1989).

Fulton et al., A 12 Megabase Restriction Map at the Cystic Fibrosis Locus, *Nucleic Acids Research 17(1)*:271–284 (1989).

Dean et al., Approaches to Localizing Disease Genes as Applied to Cystic Fibrosis, *Nucleic Acids Research 18(2)*:345–350 (1989).

Rommens et al., Physical Localization of Two DNA Markers Closely Linked to the Cystic Fibrosis Locus by Pulsed–Field Gel Electrophoresis, *Am. J. Hum. Genet. 45*:932–941 (1989).

Kerem et al., DNA Marker Haplotype Association with Pancreatic Sufficiency in Cystic Fibrosis, *Am. J. Hum. Genet. 44:827–834 (1989)*.

Estivill et al., Isolation of a New DNA Marker in Linkage Disequilibrium with Cystic Fibrosis, Situated Between J3.11 (D7S8) and IRP, *Am. J. Hum. Genet. 44*:704–710 (1989).

Iannuzzi et al., Isolation of Additional Polymorphic Clones from the Cystic Fibrosis Region, Using Chromosome Jumping from D7S8, *Am. J. Hum. Genet. 44*:695–703 (1989).

Beaudet et al., Linkage Disequilibrium, Cystic Fibrosis and Genetic Counseling, *Am. J. Hum. Genet. 44*:319–326 (1989).

Smith et al., Cystic Fibrosis: Diagnostic Testing and the Search for the Gene, *Clin. Chem. 35/7(B)*:B17–B20 (1989).

Jensen et al., Chloride Channel Expression in Cultures of Sweat Gland Epithelial Cells in Cystic Fibrosis,*J. Cell. Biol. 107(106)*:139a, Abstract No. 788 (1989).

Orr et al., In Vivo and In Vitro Phosphorylation of Apical Membrane Proteins of the T–84 Colonic Epithelial Cell Line, *J. Cell Biol. 107(6)*:493a, Abstract No. 2776 (1989).

Willumsen et al., Activation of an Apical Cl$^-$ Conductance by $Ca^{2+}$ Ionophores in Cystic Fibrosis Airway Epithelia,*Am. J. Physiol. 256*:C226–C233 (1989).

Chen et al., A cAMP–Regulated Chloride Channel in Lymphocytes That is Affected in Cystic Fibrosis, *Science 243*:657–660 (1989).

Tabcharani et al., Bicarbonate Permeability of the Outwardly Rectifying Anion Channel, *J. Membrane Biol. 112*:109–122 (1989).

Scholte et al., Immortalization of Nasal Polyp Epithelial Cells from Cystic Fibrosis Patients, *Experimental Cell Research 182*:559–571 (1989).

Koshland, D.E., Jr., The Cystic Fibrosis Gene Story, *Science 245(4922)*:1029 (1989).

Riordan et al., Identification of the Cystic Fibrosis Gene: Cloning and Characterization of Complementary DNA, *Science 245*:1066–1073 (1989).

Marx, J.L., The Cystic Fibrosis Gene is Found, *Science 245*:923–925 (1989).

Corey et al., Familial Concordance of Pancreatic Function in Cystic Fibrosis, *Journal of Pediatrics 115(2)*:274–277 (1989).

Kerem et al., Identification of the Cystic Fibrosis Gene: Genetic Analysis, *Science 245*:1073–1080 (1989).

Rommens et al., Identification of the Cystic Fibrosis Gene: Chromosome Walking and Jumping, *Science 245*:1059–1065 (1989).

Cheng et al., Increased Sulfation of Glycoconjugates by Cultured Nasal Epithelial Cells from Patients with Cystic Fibrosis, *J. Clin. Invest. 84*:68–72 (1989).

Jetten et al., Persistence of Abnormal Chloride Conductance Regulation in Transformed Cystic Fibrosis Epithelia, *Science 244*:1472–1475 (1989).

Landry, et al., Purification and Reconstitution of Chloride Channels from Kidney and Trachea,*Science 244*:1469–1472 (1989).

Drumm et al., Physical Mapping of the Cytic Fibrosis Region by Pulsed–Field Gel Electrophoresis, *Genomics 2*:346–354 (1988).

Poustka et al., A Long–Range Restriction Map Encompassing the Cystic Fibrosis Locus and Its Closely Linked Genetic Markers, *Genomics 2*:337–345 (1988).

Tsui et al., Progress Towards Cloning the Cystic Fibrosis Gene, *Phil. Trans. R. Soc. Lond. B319*:263–273 (1988).

Rommens et al., Genetic and Physical Mapping of the Chromosomal Region Containing the Cystic Fibrosis Locus, *Am. J. Hum. Genetics 43(3 Suppl.):A199 )1988)*.

Rommens et al., Identification and Regional Localization of DNA Markers on Chromosome 7 for the Cloning of the Cystic Fibrosis Gene, *Am. J. Hum. Genet. 43*:645–663 (1988).

Farrall et al., Recombinations Between IRP and Cystic Fibrosis, *Am. J. Hum. Genet. 43*:471–475 (1988).

Dean, M., Molecular and Genetic Analysis of Cystic Fibrosis, *Genomics 3*:93–99 (1988).

Riordan et al., Molecular Studies of Cultured Epithelial Cells from the Sweat Gland in Cellular and Molecular Basis of Cystic Fibrosis, (G. Mastella and P.M. Quinton, Eds.) San Francisco Press, Inc., San Francisco, CA, pp. 416–424 (1988).

Reddy et al., Electrical properties of Cultured Reabsorptive Sweat Duct Cells from Normal and Cystic . . . in Cellular and Molecular Basis of Cystic Fibrosis (G. Mastella and P.M. Quinton, Eds.) San Francisco Press, Inc., San Francisco, CA, pp. 383–393 (1988).

Short et al., λ ZAP: A Bacteriophage λ Expression Vector with In Vivo Excision Properties, *Nucleic Acids Research 16(15)*:7583–7600 (1988).

Reddy et al., Retention of Basic Electrophysiologic Properties by Human Sweat Duct Cells in Primary Culture,*In Vitro Cellular & Developmental Biology 24(9)*:905–910 (1988).

Dodge, J.A., Implications of the New Genetics for Screening for Cystic Fibrosis, *The Lancet*:672–673 (1988).

Wilson et al., Correction of the Genetic Defect in Hepatocytes from the Watanabe Heritable Hyperlipidemic Rabbit, *Proc. Natl. Acad. Sci. USA 85*:4421–4425 (1988).

Li et al., Cyclic AMP–Dependent Protein Kinase Opens Chloride Channels in Normal but not Cystic Fibrosis Airway Epithelium, *Nature 331*:358–360 (1988).

Lathrop et al., Refined Linkage Map of Chromosome 7 in the Region of the Cystic Fibrosis Gene, *Am. J. Hum. Genet. 42*:038–044 (1988).

Harris et al., Establishment of a Tissue Culture System for Epithelial Cells Derived from Human Pancreas: A Model for the Study of Cystic Fibrosis, *Journal of Cell Science 87*:695–703 (1987).

Buchwald et al., Current Status of the Genetics of Cystic Fibrosis in Genetics and Epithelial Cell Dysfunction in Cytic Fibrosis (Alan R. Liss, Inc.), pp. 19–29 (1987).

Buchwald et al., The Genetics of Cystic Fibrosis—Mid 1987, *Excerta Med. Asia Pacific Congress* 743–9 (1987).

Tsui et al., Progress Towards Cloning of the Cystic Fibrosis Gene—Identification of New DNA Markers in the 7Q31 Region, *Protides of the Biological Fluids 35*:51–54 (1987).

Estivill et al., Patterns of Polymorphism and Linkage Disequilibrium for Cystic Fibrosis, *Genomics 1*:257–263 (1987).

Zengerling et al., Mapping of DNA Markers Linked to the Cystic Fibrosis Locus on the Long Arm of Chromosome 7, *Am. J. Hum. Genet. 40*:228–236 (1987).

Beaudet et al., Prenatal Diagnosis of Cystic Fibrosis, *J. Ped. 111*:630–633 (1987).

Riordan et al., Utilization of Cultured Epithelial Cells from the Sweat Gland in Studies of the CF Defect in Genetics and Epithelial Cell Dysfunction in Cystic Fibrosis, Alan R. Liss, Inc. pp. 59–71 (1987).

Reddy et al., Lack of β–Adrenergic Responsiveness in Cells Cultured from Reabsorptive Sweat Ducts of Cystic Fibrosis (CF) Subjects, *Pediatric Pulmonology Supp. 1*:115 Abstract No. 31 (1987).

Riordan J., Reaching Between the Functional and Genetic Defects in Cystic Fibrosis, *Pediatric Pulmonology Suppl. 1*:29 (1987).

Frizzell, R.A., Cystic Fibrosis: A Disease of Ion Channels, *TINS 10(5)*:190–193 (1987).

Schoumacher et al., Phosphorylation Fails to Activate Chloride Channels from Cystic Fibrosis Airway Cells, *Nature 330*:752–754 (1987).

Meakin et al., τ–Crystallins of the Human Eye Lens: Expression Analysis of Five Members of the Gene Family, *Molecular and Cellular Biology 7(8)*:2671–2679 (1987).

Michiels et al., Derivation of Clones Close to met by Preparative Field Inversion of Gel Electrophoresis, *Science 236*:1305–1308 (1987).

Korman et al., Expression of Human Class II Major Histocompatibility Complex Antigens Using Retrovirus Vectors, *Proc. Natl. Acad. Sci. USA 84*:2150–2154 (1987).

Wahl et al., Cosmid Vectors for Rapid Genomic Walking, Restriction Mapping, and Gene Transfer, *Proc. Natl. Acad. Sci. USA 84*:2160–2164 (1987).

Estivill et al., A Candidate for the Cystic Fibrosis Locus Isolated by Selection for Methylation–Free Islands, *Nature 326*:840–845 (1987).

Collins et al., Construction of a General Human Chromosome Jumping Library, with Application to Cystic Fibrosis, *Science 235*:1046–1049 (1987).

Spence et al., Linkage of DNA Markers to Cystic Fibrosis in 26 Families, *Am. J. Hum. Genet. 39*:729–734 (1986).

Tsui et al., Genetic Analysis of Cystic Fibrosis Using Linked DNA Markers, *Am. J. Hum. Genet. 39*:720–728 (1986).

Beaudet et al. Linkage of Cystic Fibrosis to Two Tightly Linked DNA Markers: Joint Report from a Collaborative Study, *Am. J. Hum. Genet. 39*:681–693 (1986).

Scambler et al., Chromosome Mediated Gene Transfer of Six DNA Markers Linked to the Cystic Fibrosis Locus on Human Chromosome Seven, *Nucleic Acids Res. 14*:7159–7174 (1986).

Tsui et al., Mapping of the Cystic Fibrosis Locus on Chromosome 7, *Cold Spring Harbor Symp. Quant. Biol. LI*:325–335 (1986).

Schmiegelow et al., Linkage Between the Loci for Cystic Fibrosis and Paraoxonase, *Clinical Genetics 29*:374–377 (1986).

Buchwald et al., Linkage of Cystic Fibrosis to the proα2(I) Collagen Gene, COL1A2, on Chromosome 7, *Cytogenet. Cell Genet. 41*:234–239 (1986).

Boucher et al., $Na^+$ Transport in Cystic Fibrosis Respiratory Epithelia, *J. Clin. Ivest. 78*:1245–1252 (1986).

Frizzell et al., Altered Regulation of Airway Epithelial Cell Chloride Channels in Cystic Fibrosis, *Science 233*:558–560 (1986).

Welsh et al., Chloride and Potassium Channels in Cystic Fibrosis Airway Epithelia, *Nature 322*:467–470 (1986).

Tsui et al., Cystic Fibrosis: Progress in Mapping the Disease Locus Using Polymorphic DNA Markers. I., *Cytogenet. Cell Genet. 39*:299–301 (1985).

Knowlton et al., A Polymorphic DNA Marker Linked to Cystic Fibrosis is Located on Chromosome 7, *Nature 318(6044)*:380–382 (1985).

Yankaskas et al., Culture of Human Nasal Epithelial Cells on Collagen Matrix Supports, *Am. Rev. Respir. Dis. 132*:1281–1287 (1985).

Smith, M., In Vitro Mutagenesis, *Ann. Rev. Genet. 19*:423–462 (1985).

White et al., A Closely Linked Genetic Marker for Cystic Fibrosis, *Nature 318*:382–384 (1985).

Tsui et al., Cystic Fibrosis Locus Defined by a Genetically Linked Polymorphic DNA Marker, *Science 230*:1054–1057 (1985).

Stutts et al., Chloride Uptake into Cultured Airway Epithelial Cells from Cystic Fibrosis Patients and Normal Individuals, *Proc. Natl. Acad. Sci. USA 82*:6677–6681 (1985).

Collie et al., Culture of Sweat Gland Epithelial Cells from Normal Individuals and Patients with Cystic Fibrosis, *In Vitro Cellular & Developmental Biology 21(10)*:597–602 (1985).

Widdicombe et al., Cystic Fibrosis Decreases the Apical Membrane Chloride Permeability of Monolayers Cultured from Cells of Tracheal Epithelium, *Proc. Natl. Acad. Sci. USA 82*:6167–6171 (1985).

Wainwright et al., Localization of Cystic Fibrosis Locus to Human Chromosome 7cen–q22, *Nature 318*:384–385 (1985).

Taussig, L.M., Cystic Fibrosis: An Overview, *Cystic Fibrosis* (Taussig, L.M., ed.) Thieme–Stralton, N.Y., N.Y., pp. 1–9 (1984).

Sato et al., Defective Beta Adrenergic Response of Cystic Fibrosis Sweat Glands In Vivo and In Vitro, *J. Clin. Invest. 73*:1763–1771 (1984).

Brock, D.J.H., Amniotic Fluid Alkaline Phosphatase Isoenzymes in Early Prenatal Diagnosis of Cystic Fibrosis, *The Lancet*, pp. 941–943 (1983).

Feinberg et al., A Technique for Radiolabeling DNA Restriction Endouclease Fragments to High Specific Activity, *Analytical Biochemistry* 132:6–13 (1983).

Boat et al., Human Respiratory Tract Secretions, *Archives of Biochemistry and Biophysics* 177:95–104 (1976).

FIG. 1.

```
1   AATTGGAAGCAAATGACATCACAGCAGGTCAGAGAAAAAGGGTTGAGCGGCAGGCACCCA
         ↓↓
61  GAGTAGTAGGTCTCTTTGGCATTAGGAGCCCTAGCAGGACCCCAGC
                                                                    16
           M  Q  R  S  P  L  E  K  A  S  V  V  S  K  L  F
121 GCCCGAGACCATGCAGAGGTCGCAGAGCCTTGAGCCCCTCGAAAAGGCCAGCGTTGTCTCCAAACTTTTT
                                                                    36
     F  S  W  T  R  P  I  L  R  K  G  Y  R  Q  R  L  E  L  S  D
181 TTCAGCTGGACCAGACCAATTTTGAGGAAAGGATACAGACAGCGCCTGGAATTGTCAGAC
                                                                    56
     I  Y  Q  I  P  S  V  D  S  A  D  N  L  •S  E  K  L  E  R  E
241 ATATACCAAATCCCTTCTGTTGATTCTGCTGACAATCTATCTGAAAAATTGGAAAGAGAA
                                                                    76
     W  D  R  E  L  A  •S  K  K  N  P  K  L  I  N  A  L  R  R  C
301 TGGGATAGAGAGCTTGGCTTCAAAGAAAATCCTAAACTCATTAATGCCCTTCGGCGATGT
                                                                    96
     F  F  W  R │F  M  F  Y  G  I  F  L  Y  L  G │E  V  T  K  A
361 TTTTCTGGAGATTTATGTTCTATGGAATCTTTTTATATTTAGGGAAGTCACCAAAGCA
                                                                    116
    │V  Q  P  L  L│ L  G  R  I  I  A  S  Y  D  P  D  N  K  E  E
421 GTACAGCCTCTCTTACTGGGAAGAATCATAGCTTCCTATGACCCGGATAACAAGGAGGAA
```

FIG.1. con't.

```
       R   S   I   A   I   Y   L   G   I   G   L   C   L   L   F   I   V   R   T   L
481  CGCTCTATCGCGATTTATCTAGGCATAGGCTTATGCCTTCTCTTTATTGTGAGGACACTG              136

L   L   H   P   A   I   F   G   L   H   H   H   I   G   M   Q   M   R   I   A   M
541  CTCCTACACCCAGCCATTTTTGGCCTTCATCACACATTGGAATGCAGATGAGAATAGCTATG            156

F   S   L   I   Y   K   K   T   L   K   L   S   S   R   V   L   D   K   I   S
601  TTTAGTTTGATTTATAAGAAGACTTTAAAGCTGTCAAGCCGTGTTCTAGATAAAATAAGT              176

I   G   Q   L   V   S   L   L   S   N   N   L   N   K   F   D   E   G   L   A
661  ATTGGACAACTTGTTAGTCTCCTTTCCAACAACCTGAACAAATTTGATGAAGGACTTGCA              196

L   A   H   F   V   W   I   A   P   L   Q   V   A   L   L   M   G   L   I   W
721  TTGGCACATTTCGTGTGGATCGCTCCTTTGCAAGTGGCACTCCTCATGGGCTAATCTGG               216

E   L   L   Q   A   S   A   F   C   G   L   G   F   L   I   V   L   A   L   F
781  GAGTTGTTACAGGCGTCTGCCTTCTGTGGACTTGGTTTCCTGATAGTCCTTGCCCTTTTT              236

Q   A   G   L   G   R   M   M   M   K   Y   R   D   Q   R   A   G   K   I   S
841  CAGGCTGGGCTAGGGAGAATGATGATGAAGTACAGAGATCAGAGAGCTGGGAAGATCAGT              256
```

FIG.1. con't.

```
       E   R   L   V   I   T   S   E   M   I   E   N   I   Q   S   V   K   A   Y   C
 901  GAAAGACTTGTGATTACCTCAGAAATGATTGAAAATATCCAATCTGTTAAGGCATACTGC                     276

W   E   E   A   M   E   K   M   I   E   N   L   R   Q   T   E   L   K   L   T
 961  TGGGAAGAAGCAATGGAAAAAATGATTGAAAACTTAAGACAAACAGAACTGAAACTGACT                     296

R   K   A   A   Y   V   R   Y   F   N   S  │S   A   F   F   F   S   G   F   F │
1021  CGGAAGGCAGCCTATGTGAGATACTTCAATAGCTCAGCCTTCTTCTTCTCAGGGTTCTTT                     316

│V   V   F   L   S   V   L   P   Y   A   L   I │K   G   I   I   L   R   K   I │
1081  GTGGTGTTTTTATCTGTGCTTCCCTATGCACTAATCAAAGGAATCATCCTCCGGAAAATA                     336

│F   T   T   I   S   F   C   I   V   L   R   M   A   V │T   R   Q   F   P   W
1141  TTCACCACCATCTCATTCTGCATTGTTCTGCGCATGGCCGTCACTCGGCAATTTCCCTGG                     356

A   V   Q   T   W   Y   D   S   L   G   A   I   N   K   I   Q │D   F   L   Q
1201  GCTGTACAAACATGGTATGACTCTCTTGGAGCAATAAACAAAATACAGGATTTCTTACAA                     376

K   Q   E   Y   K   T   L   E   Y   N   L   T   T   T   E   V   V   M   E   N
1261  AAGCAAGAATATAAGACATTGGAATATAACTTAACGACTACAGAAGTAGTGATGGAGAAT                     396
```

FIG.1. con't.

```
       V  T  A  F  W  E  E  G  F  G  E  L  F  E  K  A  K  Q  N  N              416
1321  GTAACAGCCTTCTGGGAGGAGGGATTTGGGGAATTATTTGAGAAAGCAAAACAAT

N  N  R  K  T  S  N  G  D  D  S  L  F  F  S  N  F  S  L  L              436
1381  AACAATAGAAAAACTTCTAATGGTGATGACAGCCTCTTCTTCAGTAATTTCTCACTTCTT

G  T  P  V  L  K  D  I  N  F  K  I  E  R  G  Q  L  L  A  V              456
1441  GGTACTCCTGTCCTGAAAGATATTAATTTCAAGATAGAGAGGACAGTTGTTGGCGGTT

A  G  S  T  G  A  G  K  T  S  L  L  M  M  I  M  G  E  L  E              476
1501  GCTGGATCCACTGGAGCAGGCAAGACTTCACTTCTAATGATGATTATGGGAGAACTGGAG

P  S  E  G  K  I  K  H  S  G  R  I  S  F  C  S  Q  F  S  W              496
1561  CCTTCAGAGGGTAAAATTAAGCACACAGTGGAAGAATTTCATTCTGTTCCTCAGTTTTCCTGG

I  M  P  G  T  I  K  E  N  I  I  F  G  V  S  Y  D  E  Y  R              516
1621  ATTATGCCTGGCACCATTAAAGAAAATATCATCTTTGGTGTGTTTCCTATGATGAATATAGA

Y  R  S  V  I  K  A  C  Q  L  E  E  D  I  S  K  F  A  E  K              536
1681  TACAGAAGCGTCATCAAAGCATGCCAACTAGAAGAGGACATCTCCAAGTTTGCAGAGAAA
```

FIG.1. con't.

```
     D  N  I  V  L  G  E  G  G  I  T  L  S  G  G  Q  R  A  R  I    556
1741 GACAATATAGTTCTTGGAGAAGGTGGAATCACACTGAGTGGAGGTCAACGAGCAAGAATT

S  L  A  R  A  V  Y  K  D  A  D  L  Y  L  L  D  S  P  F  G    576
1801 TCTTTAGCAAGAGCAGTATACAAAGATGCTGATTTGTATTTATTAGACTCTCCTTTTGGA

Y  L  D  V  L  T  E  K  E  I  F  E  S  C  V  C  K  L  M  A    596
1861 TACCTAGATGTTTTAACAGAAAAAGAAATATTTGAAAGCTGTGTCTGTAAACTGATGGCT

N  K  T  R  I  L  V  T  S  K  M  E  H  L  K  K  A  D  K  I    616
1921 AACAAAACTAGGATTTTGGTCACTTCTAAAATGGAACATTTAAAGAAAGCTGACAAAATA

L  I  L  H  E  G  S  S  Y  F  Y  G  T  F  S  E  L  Q  N  L    636
1981 TTAATTTTGCATGAAGGTAGCAGCTATTTTTATGGGACATTTCAGAACTCCAAAATCTA

Q  P  D  F  S  S  K  L  M  G  C  D  S  F  D  Q  F  S  A  E    656
2041 CAGCCAGACTTTAGCTCAAAACTCATGGGATGTGATTCTTTCGACCAATTTAGTGCAGAA
```

FIG.1. con't.

```
       R  R  N  S  I  L  T  E  T  L  H  R  F  S  L  E  G  D  A  P   676
2101 AGAAGAAATTCAATCCTAACTGAGACCTTACACCGTTTCTCATTAGAAGGAGATGCTCCT

V  S  W  T  E  T  K  K  Q  S  F  K  Q  T  G  E  F  G  E  K   696
2161 GTCTCCTGGACACAGAAACAAAAACAATCTTTAAACAGACTGGAGAGTTTGGGGAAAAA

R  K  N  S  I  L  N  P  I  N  S  I  R  K  F  S  I  V  Q  K   716
2221 AGGAAGAATTCTATTCTCCAATCAACTCTATACGAAAATTTCCATTGTGCAAAAG

T  P  L  Q  M  N  G  I  E  E  D  S  D  E  P  L  E  R  R  L   736
2281 ACTCCCTTACAAATGAATGGCATCGAAGAGGATTCTGATGAGCCTTTAGAGAAGGCTG

S  L  V  P  D  S  E  Q  G  E  A  I  L  P  R  I  S  V  I  S   756
2341 TCCTTAGTACCAGATTCTGAGCAGGGAGAGGCGATACTGCCTCGCATCAGCGTGATCAGC
```

FIG.1. con't.

```
       T  G  P  T  L  Q  A  R  R  R  Q  S  V  L  N  L  M  T  H  S    776
2401 ACTGGCCCCACGCTTCAGGCACGAAGGAGGCAGTCTGTCCTGAACCTGATGACACACTCA

V  N  Q  G  Q  N  I  H  R  K  T  T  A  S  T  R  K  V  S  L    796
2461 GTTAACCAAGGTCAGAACATTCACCGAAAGACAACAGCATCCACCGAAAAGTGTCACTG

A  P  Q  A  N  L  T  E  L  D  I  Y  S  R  R  L  S  Q  E  T    816
2521 GCCCCTCAGGCAAACTTGACTGAACTGGATATATATTCAAGAAGGTTATCTCAAGAAACT

G  L  E  I  S  E  E  I  N  E  E  D  L  K  E  C  F  F  D  D    836
2581 GGCTTGGAAATAAGTGAAGAAATTAACGAAGAGACTTAAAGAGTGCTTTTTTGATGAT

M  E  S  I  P  A  V  T  T  W  N  T  Y  L  R  Y  I  T  V  H    856
2641 ATGGAGAGCATACCAGCAGTGACTACATGGAACACATACCTTCGATATATTACTGTCCAC

K  S  L  I  F  V  L  I  W  C  L  V  I  F  F  L  A  E  V  A  A    876
2701 AAGAGCTTAATTTTTGTGCTAATTTGGTGCTTAGTAATTTTTCTGGCAGAGGTGGCTGCT
```

FIG.1. con't.

```
          S  L  V  V  L  W  L  L  G  N  T  P  L  Q  D  K  G  N  S  T      896
2761 TCTTTGGTTGTGCTGTGGCTCCTTGGAAACACTCCTCTTCAAGACAAAGGGAATAGTACT

H  S  R  N  N  S  Y  A  V  I  I  T  S  T  S  S  Y  Y  V  F      916
2821 CATAGTAGAAATAACAGCTATGCAGTGATTATCACCAGCACCAGTTCGTATTATGTGTTT

Y  I  Y  V  G  V  A  D  T  L  L  A  M  G  F  F  R  G  L  P      936
2881 TACATTTACGTGGGAGTAGCCGACACTTTGCTTGCTATGGGATTCTTCAGAGGTCTACCA

L  V  H  T  L  I  T  V  S  K  I  L  H  H  K  M  L  H  S  V      956
2941 CTGGTGCATACTCTAATCACAGTGTCGAAAATTTTACACCACAAAATGTTACATTCTGTT

L  Q  A  P  M  S  T  L  N  T  L  K  A  G  I  L  N  R  F         976
3001 CTTCAAGCACCTATGTCAACCCTCAACACGTTGAAAGCAGGTGGGATTCTTAATAGATTC
```

FIG.1. con't.

```
       S   K   D   I   A   I   L   D   D   L   L   P   L   T  [ I   F   D   F   I   Q ] 996
3061   TCCAAAGATATAGCAATTTTGGATGACCTTCTGCCTCTTACCATATTTGACTTCATCCAG

[ L   L   L   I   V   I   G   A   I   A   V   V   A   V   L   Q   P   Y   I   F ] 1016
3121   TTGTTATTAATTGTGATTGGAGCTATAGCAGTTGTCGCAGTTTTACAACCCTACATCTTT

[ V   A   T   V   P   V   I   V   A   F   I   M   L   R   A   Y   F   L   Q ] T  1036
3181   GTTGCAACAGTGCCAGTGATAGTGGCTTTTATTATGTTGAGAGCATATTTCCTCCAAACC

S   Q   Q   L   K   Q   L   E   S   E   G   R   S   P   I   F   F   T   H   L   V  1056
3241   TCACAGCAACTCAAACAACTCGAAAGCCAGGAGTCCAATTTCACTCATCTTGTT

T   S   L   K   G   L   W   T   L   R   A   F   G   R   Q   P   Y   F   E   T  1076
3301   ACAAGCTTAAAAGGACTATGGACACTTCGTGCCTTCGGACGGCCAGCCTTACTTTGAAACT

L   F   H   K   A   L   N   L   H   T   A   N   W   F   L   Y   L   S   T   L  1096
3361   CTGTTCCACAAAGCTCTGAATTTACATACTGCCAACTGGTTCTTGTACCTGTCAACACTG
```

FIG.1. con't.

```
         R  W  F  Q  M  R  I  E  M  I  F  V  I  F  F  I  A  V  T  F     1116
3421    CGCTGGTTCCAAATGAGAATAGAAATGATTTTGTCATCTTCTTCATTGCTGTTACCTTC
         I  S  I  L  T  T  G  E  G  E  G  R  V  G  I  L  T  L  L  A     1136
3481    ATTTCCATTTTAACAACAGGAGAAGGAGAGTTGGTATTATCCTGACTTTAGCC
         M  N  I  M  S  T  L  Q  W  A  V  N  S  S  I  D  V  D  S  L     1156
3541    ATGAATATCATGAGTACATTGCAGTGGGCTGTAAACTCCAGCATAGATGTGGATAGCTTG
         M  R  S  V  S  R  V  F  K  F  I  D  M  P  T  E  G  K  P  T     1176
3601    ATGCGGATCTGTGAGCCGAGTCTTTAAGTTCATTGACATGCCAACAGAAGGTAAACCTACC
         K  S  T  K  P  Y  K  N  G  Q  L  S  K  V  M  I  E  N  S        1196
3661    AAGTCAACCAAACCATACAAGAATGGCCAACTCTCGAAAGTTATGATTATTGAGAATTCA
         H  V  K  K  D  D  I  W  P  S  G  G  Q  M  T  V  K  D  L  T     1216
```

FIG.1. con't.

```
3721 CACGTGAAGAAAGATGACATCTGGCCCTCAGGGGCCAAATGACTGTCAAGATCTCACA

A  K  Y  T  E  G  G  N  A  I  L  E  N  I  S  F  S  I  S  P    1236
3781 GCAAAATACACAGAAGGTGGAAATGCCATATTAGAGAACATTTCCTTCTCAATAAGTCCT

G  Q  R  V  G  L  L  G  R  T  G  S  G  K  S  T  L  L  S  A    1256
3841 GGCCAGAGGGTGGGCCTCTTGGGAAGAACTGGATCAGGGAAGAGTACTTTGTTATCAGCT

F  L  R  L  L  N  T  E  G  E  I  Q  I  D  G  V  S  W  D  S    1276
3901 TTTTGAGACTACTGAACACTGAAGGAGAAATCCAGATCGATGGTGTCTTGGATTCA

I  T  L  Q  Q  W  R  K  A  F  G  V  I  P  Q  K  V  F  I  F    1296
3961 ATAACTTTGCAACAGTGGAGGAAAGCCTTTGGAGTGATACCACAGAAAGTATTTATTTTT

S  G  T  F  R  K  N  L  D  P  Y  E  Q  W  S  D  Q  E  I  W    1316
4021 TCTGGAACATTTAGAAAAAACTTGGATCCCTATGAACAGTGGAGTGATCAAGAAATATGG
```

FIG.1. con't.

```
       K   V   A   D   E   V   G   L   R   S   V   I   E   Q   F   P   G   K   L   D    1336
4081   AAAGTTGCAGATGAGGTTGGGCTCAGATCTGTGATAGAACAGTTTCCTGGGAAGCTTGAC

F   V   L   V   D   G   G   C   V   L   S   H   G   H   K   Q   L   M   C   L    1356
4141   TTTGTCCTTGTGGATGGGGGCTGTGTCCTAAGCCATGGCCACAAGCAGTTGATGTGCTTG

A   R   S   V   L   S   K   A   K   I   L   L   L   D   E   P   S   A   H   L    1376
4201   GCTAGATCTGTTCTCAGTAAGGCGAAGATCTTGCTGCTTGATGAACCCAGTGCTCATTTG

D   P   V   T   Y   Q   I   I   R   R   T   L   K   Q   A   F   A   D   C   T    1396
4261   GATCCAGTAACATACCAAATAATTAGAAGAACTCTAAAACAAGCATTTGCTGATTGCACA

V   I   L   C   E   H   R   I   E   A   M   L   E   C   Q   Q   F   L   V   I    1416
4321   GTAATTCTCTGTGAACACAGGATAGAAGCAATGCTGGAATGCCAACAATTTTTGGTCATA

E   E   N   K   V   R   Q   Y   D   S   I   Q   K   L   L   N   E   R   S   L    1436
```

FIG.1. con't.

```
4381 GAAGAGAACAAAGTGCGGCAGTACGATTCCATCCAGAAACTGCTGAACGAGAGGAGCCTC
       F  R  Q  A  I  S  P  S  D  R  V  K  L  F  P  H  R  N  S  *  1456
4441 TTCCGGCAAGCCATCAGCCCCTCCGACAGGGTGAAGCTCTTTCCCCACCGGAACTCAAGC
      K  C  S  K  P  Q  I  A  A  L  K  E  E  T  E  E  E  V  Q     1476
4501 AAGTGCAAGTCTAAGCCCCAGATTGCTGCTCTGAAAGAGGAGACAGAAGAGGAGGTGCAA
      D  T  R  L  =                                                1480
4561 GATACAAGGCTTTAGAGAGCAGCATAAATGTTGACATGGACATTGCTCATGGAATTGG
4621 AGCTCGTGGGACAGTCACCTCATGGAATTAAGTGAGCTCGTGGAACAGTTACCTCTGCCTCAG
4681 AAAACAAGGATGAATTAAGTTTTTTTTAAAAAAGAAACATTTGGTAAGGGAATTGAGG
4741 ACACTGATATGGGTCTTGATAATGGCTTCCTGGTTTTGCAAGCCAGATTTCCTGAAAGGTAC
4801 TTCAAATCCTTGAAGATTTACCACTTGTGTTTTGCAAGCCAGATTTCCTGAAAACCCTT
4861 GCCATGTGCTAGTAATTGGAAAGGCAGCTCTAAATGTCAATCAGCCTAGTTGATCAGCTT
4921 ATTGTCTAGTGAACTCGTTAATTGTAGTGTTGGAGAAGAACTGAAATCATACTTCTTA
4981 GGGTTATGATTAAGTAATGATAATCTCAGCGTTTATATAAGCTTGTATTCCT
```

FIG.1. con't.

```
5041  TTTCTCCTCCTCCCCATGATGTTTAGAAACACAACTATATTGTTTGCTAAGCATTCCA
5101  ACTATCTCATTCCAAGCAAGTATTAGAATACCACAGGAACCAAGACTGCACATCAAA
5161  ATATGCCCCATTCAACATCTAGTGAGCAGTCAGGAAAGAGAACTTCCAGATCCTGAAAT
5221  CAGGGTTAGTATTGTCCAGGTCTACCAAAATCAATATTTCAGATAATCACAATACAT
5281  CCCTTACCTGGGAAAGGGCTGTTATAATCTTTCACAGGGACAGGATGGTTCCCTTGATG
5341  AAGAAGTTGATATGCCTTTTCCCAACTCCAGAAAGTGACAAGCTCACAGACCTTTGAACT
5401  AGAGTTTAGCTGGAAAAGTATGTTAGTGCAAATTGTCACAGGACAGCCCTTCTTTCCACA
5461  GAAGCTCCAGGTAGAGGGTGTGTAAGTAGATAGGCCATGGGCACTGTGGGTAGACACACA
5521  TGAAGTCCAAGCATTAGATGTATAGGTTGATGGTGGTATGTTTTCAGGCTAGATGTATG
5581  TACTTCATGCTGTCTACTAAGAGAGAATGAGAGACACTGAAGAAGCACCAATCATG
5641  AATTAGTTTTATATGCTTCTGTTTTATAATTTTGTGAAGCAAAATTTTTCTCTAGGAAA
5701  TATTTATTTTAATAATGTTTCAAACATATATTACAATGCTGTATTTTAAAAGAATGATTA
5761  TGAATTACATTGTATAAATAATTTTTATATTTGAAATATTGACTTTTATGGCACTAG
```

FIG.1. con't.

```
5821  TATTTTTATGAAATATTATGTTAAAACTGGGACACAGGGGAGAACCTAGGGTGATATTAACC
5881  AGGGGCCATGAATCACCCTTTTGGTCTCTGGAGGAAGCCCTTGGGGCTGATCGAGTTGTTGCC
5941  CACAGCTGTATGATTCCCAGCCAGACACAGCCTCTTAGATGCAGTTCTGAAGAAGATGGT
6001  ACCACCAGTCTGACTGTTTCCATCAAGGGTACACTGCCTTCTCAACTCCAAACTGACTCT
6061  TAAGAAGACTGCATTATATTTATTACTGTAAGAAAATATCACTTGTCAATAAAATCCATA
6121  CATTTGTGT(A)n
```

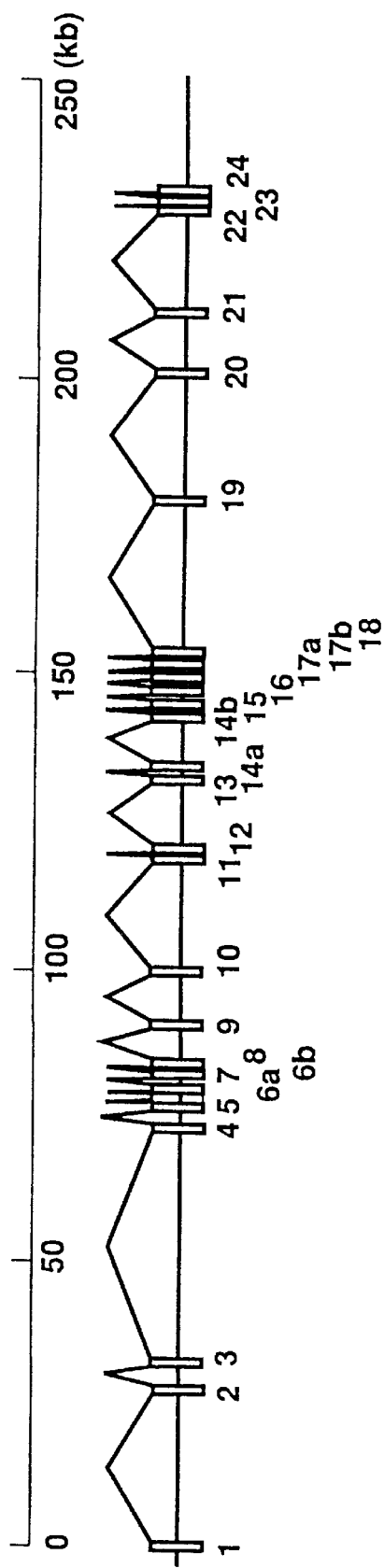
FIG. 2a. CF GENE
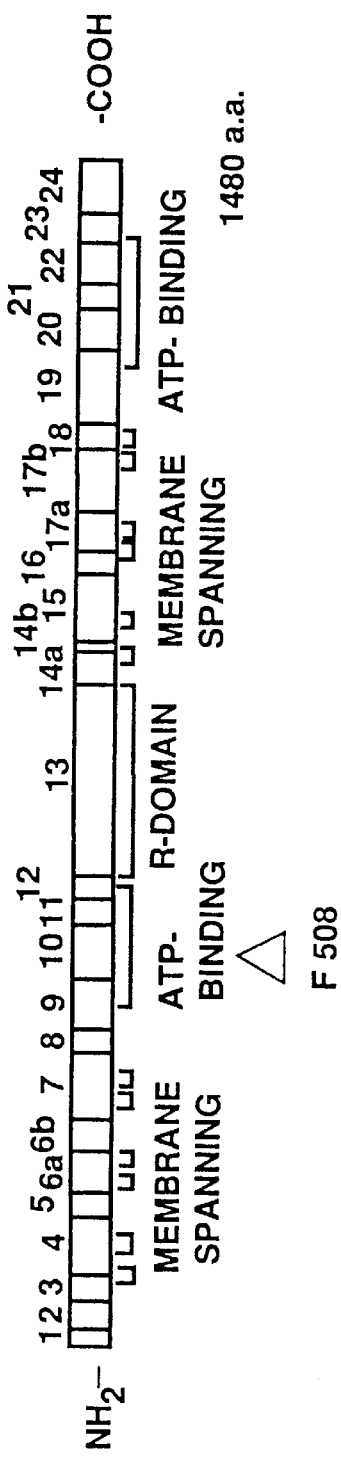
FIG. 2b. CFTR

FIG.3.

```
                                                                                    -10
Exon 6b:  AGATCAGAGAGCTGGGAAGATCAGTGAAAGACTTGTGATTACCTCAG
          876
          -35
          TTGACA--------(17±bp)--------TATAAT
                      C  G  C
                      930 933 936
          AAATGATTGAAAATATCCAATCTGTTAAGGCATACTGCTGGGAAGAAGCAATGGAAA AAATGATTGAAAACTTAAGACAAACAGAACTGAAACTGACTCGGAAGG
                                                        1027
```

RNA ANALYSIS

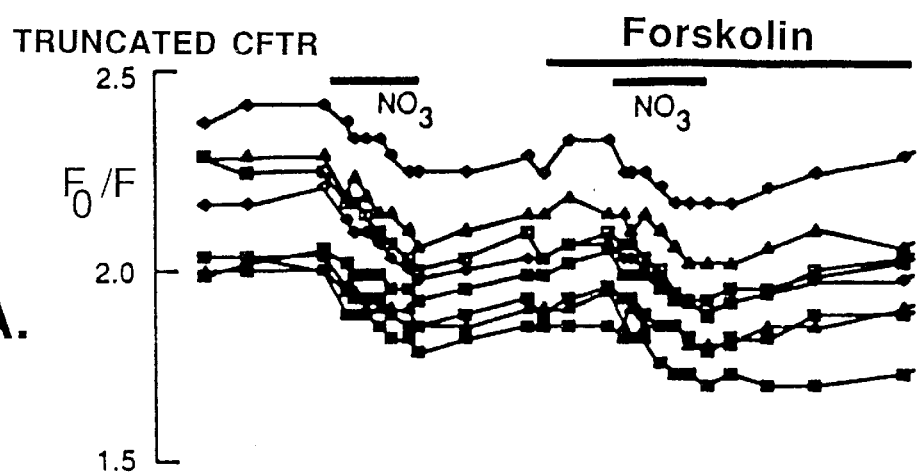
FIG 15.A.
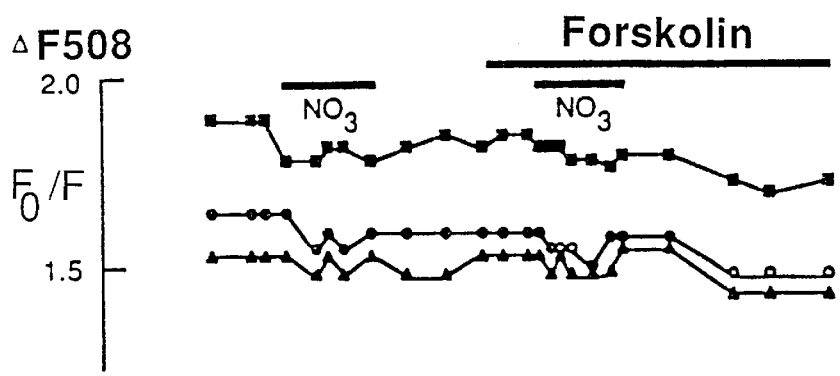
FIG 15.B.
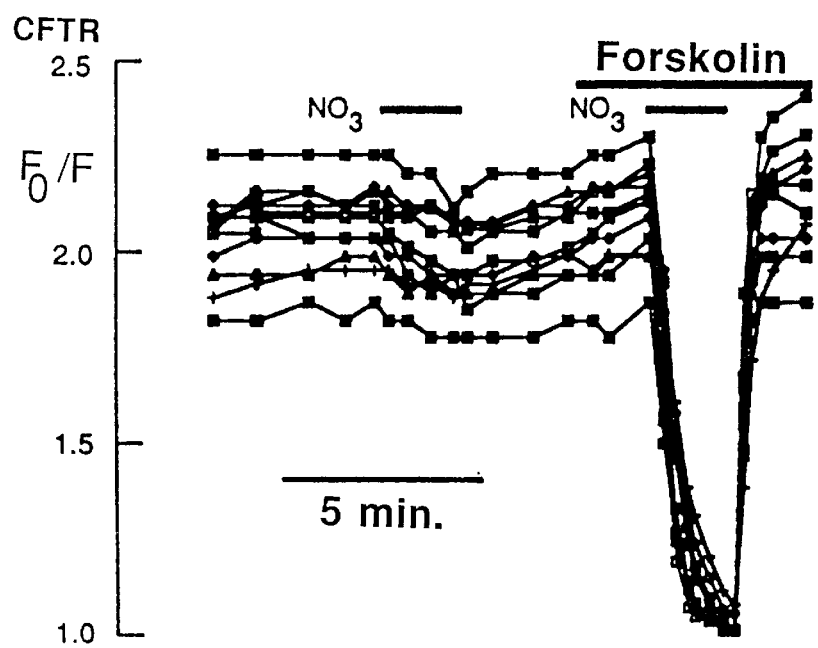
FIG 15.C.

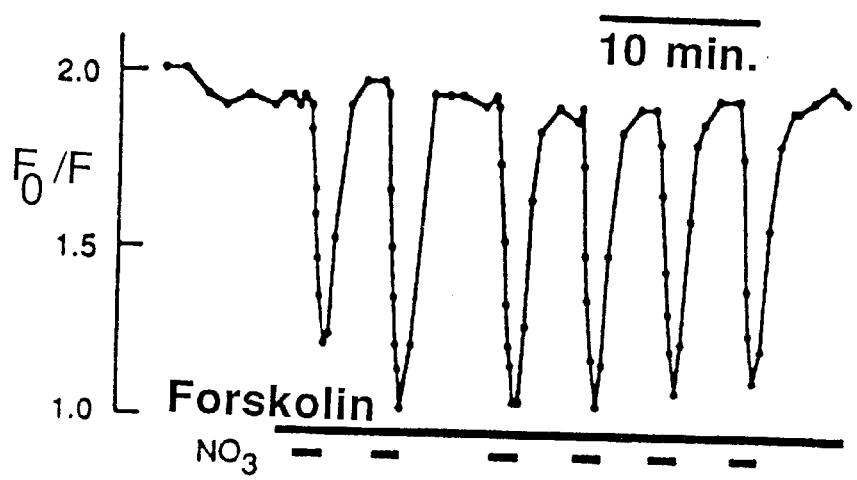
FIG 15.D.
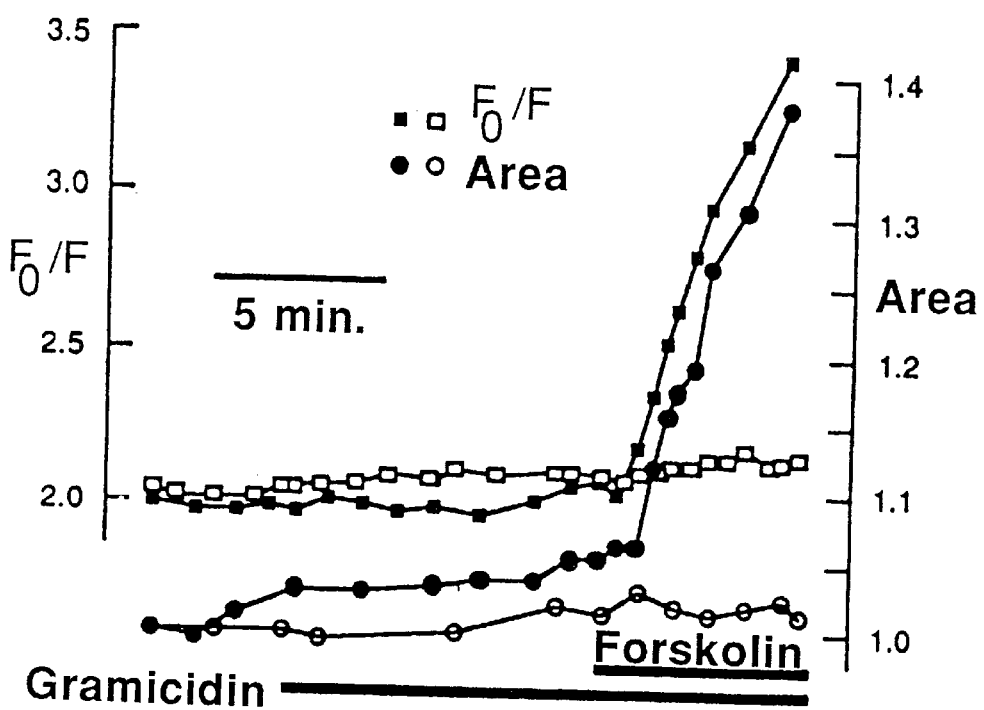
FIG 15.E.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 6130 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (F) TISSUE TYPE: Epithelial
        (G) CELL TYPE: Epithelial cell (vii) IMMEDIATE SOURCE:

(B) CLONE: mutant CF gene (viii) POSITION IN GENOME:
    (A) CHROMOSOME/SEGMENT: 7
    (B) MAP POSITION: XV2C
    (C) UNITS: bp (xi) SEQUENCE DESCRIPTION: SEQ ID NO:1:

```
AATTGGAAGC AAATGACATC ACAGCAGGTC AGAGAAAAAG GGTTGAGCGG CAGGCACCCA      60

GAGTAGTAGG TCTTTGGCAT TAGGAGCTTG AGCCCAGACG GCCCTAGCAG GGACCCCAGC     120

GCCCGAGAGA CCATGCAGAG GTCGCCTCTG GAAAAGGCCA GCGTTGTCTC CAAACTTTTT     180

TTCAGCTGGA CCAGACCAAT TTTGAGGAAA GGATACAGAC AGCGCCTGGA ATTGTCAGAC     240

ATATACCAAA TCCCTTCTGT TGATTCTGCT GACAATCTAT CTGAAAAATT GGAAAGAGAA     300

TGGGATAGAG AGCTGGCTTC AAAGAAAAAT CCTAAACTCA TTAATGCCCT TCGGCGATGT     360

TTTTTCTGGA GATTTATGTT CTATGGAATC TTTTTATATT TAGGGAAGT CACCAAAGCA      420

GTACAGCCTC TCTTACTGGG AAGAATCATA GCTTCCTATG ACCCGGATAA CAAGGAGGAA     480

CGCTCTATCG CGATTTATCT AGGCATAGGC TTATGCCTTC TCTTTATTGT GAGGACACTG     540

CTCCTACACC CAGCCATTTT TGGCCTTCAT CACATTGGAA TGCAGATGAG AATAGCTATG     600

TTTAGTTTGA TTTATAAGAA GACTTTAAAG CTGTCAAGCC GTGTTCTAGA TAAAATAAGT     660

ATTGGACAAC TTGTTAGTCT CCTTTCCAAC AACCTGAACA AATTTGATGA AGGACTTGCA     720

TTGGCACATT TCGTGTGGAT CGCTCCTTTG CAAGTGGCAC TCCTCATGGG GCTAATCTGG     780

GAGTTGTTAC AGGCGTCTGC CTTCTGTGGA CTTGGTTTCC TGATAGTCCT TGCCCTTTTT     840

CAGGCTGGGC TAGGGAGAAT GATGATGAAG TACAGAGATC AGAGAGCTGG GAAGATCAGT     900

GAAAGACTTG TGATTACCTC AGAAATGATT GAAAATATCC AATCTGTTAA GGCATACTGC     960

TGGGAAGAAG CAATGGAAAA AATGATTGAA ACTTAAGAC AAACAGAACT GAAACTGACT     1020

CGGAAGGCAG CCTATGTGAG ATACTTCAAT AGCTCAGCCT TCTTCTTCTC AGGGTTCTTT     1080

GTGGTGTTTT TATCTGTGCT TCCCTATGCA CTAATCAAAG GAATCATCCT CCGGAAAATA     1140

TTCACCACCA TCTCATTCTG CATTGTTCTG CGCATGGCGG TCACTCGGCA ATTTCCCTGG     1200

GCTGTACAAA CATGGTATGA CTCTCTTGGA GCAATAAACA AAATACAGGA TTTCTTACAA     1260

AAGCAAGAAT ATAAGACATT GGAATATAAC TTAACGACTA CAGAAGTAGT GATGGAGAAT     1320

GTAACAGCCT TCTGGGAGGA GGGATTTGGG GAATTATTTG AGAAAGCAAA ACAAAACAAT     1380

AACAATAGAA AAACTTCTAA TGGTGATGAC AGCCTCTTCT TCAGTAATTT CTCACTTCTT     1440

GGTACTCCTG TCCTGAAAGA TATTAATTTC AAGATAGAAA GAGGACAGTT GTTGGCGGTT     1500

GCTGGATCCA CTGGAGCAGG CAAGACTTCA CTTCTAATGA TGATTATGGG AGAACTGGAG     1560

CCTTCAGAGG GTAAAATTAA GCACAGTGGA AGAATTTCAT TCTGTTCTCA GTTTTCCTGG     1620

ATTATGCCTG GCACCATTAA AGAAAATATC ATCTTTGGTG TTTCCTATGA TGAATATAGA     1680

TACAGAAGCG TCATCAAAGC ATGCCAACTA GAAGAGGACA TCTCCAAGTT TGCAGAGAAA     1740

GACAATATAG TTCTTGGAGA AGGTGGAATC ACACTGAGTG GAGGTCAACG AGCAAGAATT     1800

TCTTTAGCAA AGGCAGTATA CAAAGATGCT GATTTGTATT TATTAGACTC TCCTTTTGCA     1860

TACCTAGATG TTTTAACAGA AAAAGAAATA TTTGAAAGCT GTGTCTGTAA ACTGATGGCT     1920

AACAAAACTA GGATTTTGGT CACTTCTAAA ATGGAACATT TAAAGAAAGC TGACAAAATA     1980

TTAATTTTGC ATGAAGGTAG CAGCTATTTT TATGGGACAT TTTCAGAACT CCAAAATCTA     2040

CAGCCAGACT TTAGCTCAAA ACTCATGGGA TGTGATTCTT TCGACCAATT TAGTGCAGAA     2100
```

-continued

```
AGAAGAAATT CAATCCTAAC TGAGACCTTA CACCGTTTCT CATTAGAAGG AGATGCTCCT      2160

GTCTCCTGGA CAGAAACAAA AAAACAATCT TTTAAACAGA CTGGAGAGTT TGGGGAAAAA      2220

AGGAAGAATT CTATTCTCAA TCCAATCAAC TCTATACGAA AATTTTCCAT TGTGCAAAAG      2280

ACTCCCTTAC AAATGAATGG CATCGAAGAG GATTCTGATG AGCCTTTAGA GAGAAGGCTG      2340

TCCTTAGTAC CAGATTCTGA GCAGGGAGAG GCGATACTGC CTCGCATCAG CGTGATCAGC      2400

ACTGGCCCCA CGCTTCAGGC ACGAAGGAGG CAGTCTGTCC TGAACCTGAT GACACACTCA      2460

GTTAACCAAG GTCAGAACAT TCACCGAAAG ACAACAGCAT CCACACGAAA AGTGTCACTG      2520

GCCCCTCAGG CAAACTTGAC TGAACTGGAT ATATATTCAA GAAGGTTATC TCAAGAAACT      2580

GGCTTGGAAA TAAGTGAAGA AATTAACGAA GAAGACTTAA AGGAGTGCCT TTTTGATGAT      2640

ATGGAGAGCA TACCAGCAGT GACTACATGG AACACATACC TTCGATATAT TACTGTCCAC      2700

AAGAGCTTAA TTTTTGTGCT AATTTGGTGC TTAGTAATTT TTCTGGCAGA GGTGGCTGCT      2760

TCTTTGGTTG TGCTGTGGCT CCTTGGAAAC ACTCCTCTTC AAGACAAAGG GAATAGTACT      2820

CATAGTAGAA ATAACAGCTA TGCAGTGATT ATCACCAGCA CCAGTTCGTA TTATGTGTTT      2880

TACATTTACG TGGGAGTAGC CGACACTTTG CTTGCTATGG GATTCTTCAG AGGTCTACCA      2940

CTGGTGCATA CTCTAATCAC AGTGTCGAAA ATTTTACACC ACAAAATGTT ACATTCTGTT      3000

CTTCAAGCAC CTATGTCAAC CCTCAACACG TTGAAAGCAG GTGGGATTCT TAATAGATTC      3060

TCCAAAGATA TAGCAATTTT GGATGACCTT CTGCCTCTTA CCATATTTGA CTTCATCCAG      3120

TTGTTATTAA TTGTGATTGG AGCTATAGCA GTTGTCGCAG TTTTACAACC CTACATCTTT      3180

GTTGCAACAG TGCCAGTGAT AGTGGCTTTT ATTATGTTGA GAGCATATTT CCTCCAAACC      3240

TCACAGCAAC TCAAACAACT GGAATCTGAA GGCAGGAGTC CAATTTTCAC TCATCTTGTT      3300

ACAAGCTTAA AAGGACTATG GACACTTCGT GCCTTCGGAC GGCAGCCTTA CTTTGAAACT      3360

CTGTTCCACA AAGCTCTGAA TTTACATACT GCCAACTGGT TCTTGTACCT GTCAACACTG      3420

CGCTGGTTCC AAATGAGAAT AGAAATGATT TTTGTCATCT TCTTCATTGC TGTTACCTTC      3480

ATTTCCATTT TAACAACAGG AGAAGGAGAA GGAAGAGTTG GTATTATCCT GACTTTAGCC      3540

ATGAATATCA TGAGTACATT GCAGTGGGCT GTAAACTCCA GCATAGATGT GGATAGCTTG      3600

ATGCGATCTG TGAGCCGAGT CTTTAAGTTC ATTGACATGC CAACAGAAGG TAAACCTACC      3660

AAGTCAACCA AACCATACAA GAATGGCCAA CTCTCGAAAG TTATGATTAT TGAGAATTCA      3720

CACGTGAAGA AAGATGACAT CTGGCCCTCA GGGGGCCAAA TGACTGTCAA AGATCTCACA      3780

GCAAAATACA CAGAAGGTGG AAATGCCATA TTAGAGAACA TTTCCTTCTC AATAAGTCCT      3840

GGCCAGAGGG TGGGCCTCTT GGGAAGAACT GGATCAGGGA AGAGTACTTT GTTATCAGCT      3900

TTTTTGAGAC TACTGAACAC TGAAGGAGAA ATCCAGATCG ATGGTGTGTC TTGGGATTCA      3960

ATAACTTTGC AACAGTGGAG GAAAGCCTTT GGAGTGATAC CACAGAAAGT ATTTATTTTT      4020

TCTGGAACAT TTAGAAAAAA CTTGGATCCC TATGAACAGT GGAGTGATCA AGAAATATGG      4080

AAAGTTGCAG ATGAGGTTGG GCTCAGATCT GTGATAGAAC AGTTTCCTGG AAGCTTGAC      4140

TTTGTCCTTG TGGATGGGGG CTGTGTCCTA AGCCATGGCC ACAAGCAGTT GATGTGCTTG      4200

GCTAGATCTG TTCTCAGTAA GGCGAAGATC TTGCTGCTTG ATGAACCCAG TGCTCATTTG      4260

GATCCAGTAA CATACCAAAT AATTAGAAGA ACTCTAAAAC AAGCATTTGC TGATTGCACA      4320

GTAATTCTCT GTGAACACAG GATAGAAGCA ATGCTGGAAT GCCAACAATT TTTGGTCATA      4380

GAAGAGAACA AAGTGCGGCA GTACGATTCC ATCCAGAAAC TGCTGAACGA GAGGAGCCTC      4440

TTCCGGCAAG CCATCAGCCC CTCCGACAGG GTGAAGCTCT TCCCCCACCG GAACTCAAGC      4500
```

-continued

```
AAGTGCAAGT CTAAGCCCCA GATTGCTGCT CTGAAAGAGG AGACAGAAGA AGAGGTGCAA    4560

GATACAAGGC TTTAGAGAGC AGCATAAATG TTGACATGGG ACATTTGCTC ATGGAATTGG    4620

AGCTCGTGGG ACAGTCACCT CATGGAATTG GAGCTCGTGG AACAGTTACC TCTGCCTCAG    4680

AAAACAAGGA TGAATTAAGT TTTTTTTTAA AAAAGAAACA TTTGGTAAGG GGAATTGAGG    4740

ACACTGATAT GGGTCTTGAT AAATGGCTTC CTGGCAATAG TCAAATTGTG TGAAAGGTAC    4800

TTCAAATCCT TGAAGATTTA CCACTTGTGT TTTGCAAGCC AGATTTTCCT GAAAACCCTT    4860

GCCATGTGCT AGTAATTGGA AAGGCAGCTC TAAATGTCAA TCAGCCTAGT TGATCAGCTT    4920

ATTGTCTAGT GAAACTCGTT AATTTGTAGT GTTGGAGAAG AACTGAAATC ATACTTCTTA    4980

GGGTTATGAT TAAGTAATGA TAACTGGAAA CTTCAGCGGT TTATATAAGC TTGTATTCCT    5040

TTTTCTCTCC TCTCCCCATG ATGTTTAGAA ACACAACTAT ATTGTTTGCT AAGCATTCCA    5100

ACTATCTCAT TTCCAAGCAA GTATTAGAAT ACCACAGGAA CCACAAGACT GCACATCAAA    5160

ATATGCCCCA TTCAACATCT AGTGAGCAGT CAGGAAAGAG AACTTCCAGA TCCTGGAAAT    5220

CAGGGTTAGT ATTGTCCAGG TCTACCAAAA ATCTCAATAT TTCAGATAAT CACAATACAT    5280

CCCTTACCTG GGAAAGGGCT GTTATAATCT TTCACAGGGG ACAGGATGGT TCCCTTGATG    5340

AAGAAGTTGA TATGCCTTTT CCCAACTCCA GAAAGTGACA AGCTCACAGA CCTTTGAACT    5400

AGAGTTTAGC TGGAAAAGTA TGTTAGTGCA AATTGTCACA GGACAGCCCT TCTTTCCACA    5460

GAAGCTCCAG GTAGAGGGTG TGTAAGTAGA TAGGCCATGG GCACTGTGGG TAGACACACA    5520

TGAAGTCCAA GCATTTAGAT GTATAGGTTG ATGGTGGTAT GTTTTCAGGC TAGATGTATG    5580

TACTTCATGC TGTCTACACT AAGAGAGAAT GAGAGACACA CTGAAGAAGC ACCAATCATG    5640

AATTAGTTTT ATATGCTTCT GTTTTATAAT TTTGTGAAGC AAAATTTTTT CTCTAGGAAA    5700

TATTTATTTT AATAATGTTT CAAACATATA TTACAATGCT GTATTTTAAA AGAATGATTA    5760

TGAATTACAT TTGTATAAAA TAATTTTTAT ATTTGAAATA TTGACTTTTT ATGGCACTAG    5820

TATTTTTATG AAATATTATG TTAAAACTGG GACAGGGGAG AACCTAGGGT GATATTAACC    5880

AGGGGCCATG AATCACCTTT TGGTCTGGAG GGAAGCCTTG GGGCTGATCG AGTTGTTGCC    5940

CACAGCTGTA TGATTCCCAG CCAGACACAG CCTCTTAGAT GCAGTTCTGA AGAAGATGGT    6000

ACCACCAGTC TGACTGTTTC CATCAAGGGT ACACTGCCTT CTCAACTCCA AACTGACTCT    6060

TAAGAAGACT GCATTATATT TATTACTGTA AGAAAATATC ACTTGTCAAT AAAATCCATA    6120

CATTTGTGTA                                                          6130
```

STABLE HETEROLOGOUS PROPAGATION CFTR PROTEIN VARIANT CDNA

This application is a continuation-in-part of U.S. application Ser. No. 07/401,609, filed Aug. 31, 1989 now abandoned, which is a continuation of U.S. application Ser. No. 07/399,945, filed Aug. 24, 1989, now abandoned, which is a continuation of U.S. patent application Ser. No. 07/396,894, filed Aug. 22, 1989, now abandoned.

FIELD OF THE INVENTION

This invention relates to modifications in the cDNA of full length cystic fibrosis transmembrane conductance regulator protein (CFTR) which facilitates propagation and/or expression in heterologous systems.

BACKGROUND OF THE INVENTION

Cystic fibrosis (CF) is the most common, life-threatening, autosomal recessive disease in the Caucasian population. Approximately 1 in 2,500 live births is affected by this genetic disorder. Obstructive lung disease, pancreatic enzyme insufficiency and elevated sweat electrolytes are the hallmarks for CF but the severity of these symptoms vary from patient to patient. Patients with CF usually die at an early age due to lung infection. With recent advances in clinical treatments, which are directed against the symptoms, the mean survival age for patients has increased to 26 years.

Despite intensive research efforts for the past fifty years, the basic defect in CF remains to be speculative. It is generally believed that the heavy mucus found in the respiratory tracts and the blockage of exocrine secretion from the pancreas are due to imbalance in water secretion which is the consequence of a defect in the regulation of ion transport in the epithelial cells.

The precise localization of the CF locus on the long arm of chromosome 7, region q31, facilitated the recent isolation of the responsible gene. The CF gene spans 250 kilobase pairs (kb) of DNA and encode a mRNA of about 6,500 nucleotides in length. The CFTR-gene is disclosed and claimed in U.S. application Ser. No. 401,609 filed Aug. 31, 1989. That application is co-owned by the applicant of this application.

Expression of this gene could be observed in a variety of tissues that are affected in CF patients, for example, lung, pancreas, liver, sweat gland and nasal epithelia. An open reading frame spanning 1480 amino acids could be deduced from the overlapping cDNA clones isolated. The putative protein as noted is called "Cystic Fibrosis Transmembrane Conductance Regulator" or CFTR for short, to reflect its possible role in the cells. The predicted molecular mass of CFTR is about 170,000.

Based on sequence alignment with other proteins of known functions, CFTR is thought to be a membrane-spanning protein which can function as a cyclic AMP-regulated chloride channel. The internal sequence identity between the first and second half of CFTR resembles the other prokaryotic and eukaryotic transport proteins, most notably, the mammalian P-glycoprotein.

The most frequent mutant allele of the CF gene involves a three base pair (bp) deletion which results in the deletion of a single amino acid residue (phenylalanine) at position 508, within the first ATP-binding domain of the predicted polypeptide. Although this mutation (ΔF508) accounts for about 70% of all CF chromosomes, there is marked difference in its proportion among different populations. The remaining 30% of mutations in the CF gene appear to be heterogeneous and most of them are rare, with some represented by only single examples, as referenced in applicant's Canadian patent application filed Jul. 9, 1990.

The mutation screening study confirms that the ATP-binding domains detected by sequence alignment is important for CFTR function as multiple, different mutations have been found for many of the highly conserved amino acid residues in these regions. The locations of the various mutations also identified other functionally important regions in CFTR. There is, for example, a section three bp deletion resulting in the omission of an isoleucine residue at position 506 or 507 of the putative protein. While amino acid substitutions at these positions are apparently not disease-causing, this observation argues that the length of the peptide is more critical than the actual amino acid residue in the 506–508 region. Further, the existence of a large number of nonsense, frameshift as well as mRNA splicing mutations in the CF gene implies that absence of CFTR is not incompatible with life.

The varied symptoms among different CF patients suggest that disease severity is at least in part related to the mutations in the CF gene. Such association, which is expected to be concordant among patients within the same family, as they should have the same genotype at the CF locus, is observed for pancreatic function. Approximately 85% of CF patients are severely deficient in pancreatic enzyme secretion, thus diagnosed as pancreatic insufficient (PI), and the other 15% have sufficient enzyme, thus pancreatic sufficient (PS). Family studies showed that there was almost complete concordance of the pancreatic status among patients within the same family, leading to the suggestion that PI and PS are predisposed by the patients' genotypes. Subsequent studies showed that patients homozygous for the ΔF508 mutation were almost exclusively PI. This information may be useful in disease prognosis.

There are other mutations that would be classified in the same group as ΔF508, the so-called severe mutant alleles with respect to pancreatic function. In contrast, patients with one or two copies of other class (i.e. mild) of alleles are expected to be PS. Meconium ileus which is observed in about 30% of CF patients appears to be a clinical variation of PI and not directly determined by the CF genotype. Other clinical manifestations are more complicated and no apparent association has yet been detected.

With the identification of the CF gene, a better understanding of the basic defect and pathophysiology of the disease can now be attained. Progress and advance are being made in studies of the regulatory mechanisms governing the expression of this gene, and of the biosynthesis and subcellular localization of the protein (through generation of antibodies against various parts of the protein). In addition, it is important to develop effective assay systems for the function of CFTR. This information may be useful in development of rational therapies, including gene therapy.

In order to obtain a DNA sequence containing the entire coding region of CFTR, it is necessary to construct a full-length cDNA from overlapping clones previously isolated. A major difficulty has been encountered in the process, however. As the various proportions of the full-length cDNA are being linked together by standard procedures; i.e., restriction enzyme cutting and ligation, with plasmid vector in *Escherichia coli,* frequent sequence rearrangement has been detected in the resulting construct.

For purposes of better understanding of the regulatory functions of the CFTR protein and also for purposes of gene and drug therapy, it is useful to be able, in a commercial way, to propagate and express the normal CFTR gene and various mutant CFTR genes in a variety of hosts which include bacteria, yeast, molds, plant and animal cells and the like.

Although propagation and expression of the cDNA sequence for the CFTR gene can be achieved in some vehicles, there are, however, the aforementioned difficulties in obtaining stable propagation of the cDNA in some types of bacteria, particularly E. coli. It is thought that the cDNA contains sequence portions which, when propagated in the bacteria, result in a toxic effect which is countered by lack of propagation of the cDNA in the microorganism.

SUMMARY OF THE INVENTION

We have discovered that a modification of a cDNA repeat sequence in exon 6 of the CFTR gene without modifying the amino acids encoded by the changed codons facilitates propagation and/or expression of the CFTR protein in living cells and in particular bacterial cells.

According to an aspect of the present invention, a modified DNA sequence derived from a gene coding for cystic fibrosis transmembrane conductance regulator (CFTR) protein, the gene having at least 27 exons of which normal cDNA codes for CFTR protein, the normal cDNA including exons 6a and 6b wherein exon 6b includes a 13 bp repeat, the modified DNA sequence comprises at least one of the 13 bp repeats of exon 6b having one or more normal nucleotides of the 13 bp repeat substituted with an alternate nucleotide which continues to code for a corresponding normal amino acid.

According to another aspect of the present invention, a DNA construct for use in a recombinant vector comprises the modified cDNA.

According to a another aspect of the present invention, a vector which comprises the DNA construct and a promoter sequence for the DNA construct.

According to futher aspect of the present invention, a host cell for producing CFTR protein, the host cell comprises the above vector whereby expression of the vector in the host cell produces CFTR protein.

According to another aspect of the present invention, a CFTR protein isolated and purified from culture of the host cell.

According to a further aspect of the present invention, a mammalian cell transfected with the above vector to enhance Cl⁻ conductance through a cell wall.

BRIEF DESCRIPTION OF DRAWINGS

FIG. 1 is the nucleotide sequence of the CFTR gene and the amino acid sequence of the CFTR protein as shown in FIG. 2 of Riordan et al. (1989) with added solid triangles indicating candidate nucleotide positions for silent mutation.

FIGS. 2(a) and 2(b) are schematic diagrams of the CF gene and its protein product. (a) Gene structure with exons represented by open boxes; and (b) Computer-predicted primary structure of CFTR.

FIG. 3 is a DNA sequence of exon 6b. The nucleotide positions (877–1002) for exon 6 correspond to the previous cDNA numbering scheme (Riordan et al 1989). The 13 bp direct repeats are underlined. The consensus prokaryotic transcription signals (at positions −35 and −10) are included for comparison. The modified nucleotides in pCOF-1; pBQ6.2 and pBQ4.7 are shown underneath.

The autoradiograph shows examples of the hybridization results with the CFTR cDNA probe. As indicated, the first lane on the left, LTK⁻, contains mouse genome DNA. The second and third lanes, indicated as 2a-4A and 2a-4C, contain DNA from HAT-resistant clones obtained by transfection with pSTK7 only. The remaining lanes contain DNA from HAT-resistant clones obtained by co-transfection with pSTK7 and pCOF-1, 4th through 11th lanes (from left to right), and pSTK7 and pCONZ, 3 lanes at the far right. Individual clone names are indicated. Molecular weight markers are shown on the left (in kb). The two diagnostic bands in clones shown in 4th, 6th, 8th, 9th and 14th lanes are 2.3 kb (the 5' end of the CFTR gene plus the expression vector, promoter sequence) and 2.5 kb (CFTR internal segment).

Figure 12:
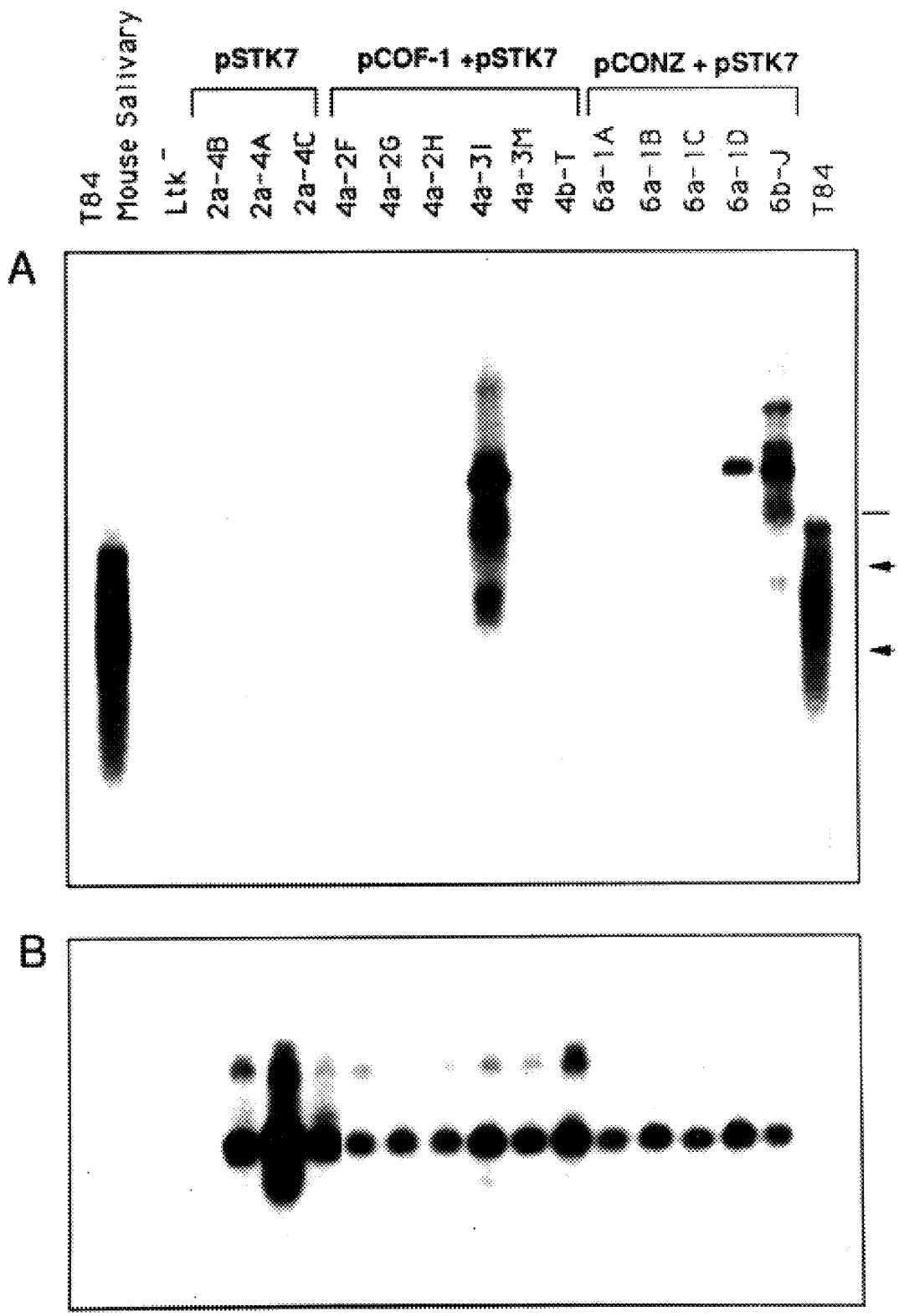

FIG. 12 is RNA hybridization analysis. Total RNA was extracted from each cell line, purified through CsCl gradient centrifugation, and separated on a 1.0% formaldehyde agarose gel in MOPS-acetate buffer. The samples were transferred to Zetabind (Bio-Rad Labs) membrane and hybridized sequentially with radioactively labeled CFTR cDNA (panel A) and the TK cDNA probe (panel B). As indicated, the samples in the lanes at the far left and far right were prepared from the colonic cell line T84. The second lane (from left) contained RNA from fresh mouse salivary tissue; and the third lane (from left) contained RNA from untransfected LTK-cells. The 4th through 6th lanes (from left) contain RNA prepared from independent clones generated from pSTK7 transfection, the 7th through 12th lanes from co-transfection with pSTK7 and pCOF-1; and the 13th through 17th lanes from co-transfection with pSTK7 and pCONz, as indicated. The 28 S and 18S rRNA bands are indicated by the arrows at the right. The position anticipated for the full-length transcript (6.2 kb) is also marked. The lanes of panel B correspond to those of panel A. The expected transcript for the HSVTK gene is 2.2 kb, as observed in panel B. The expected transcript for the HSV YK gene is 2.2 kb.

Figure 13:
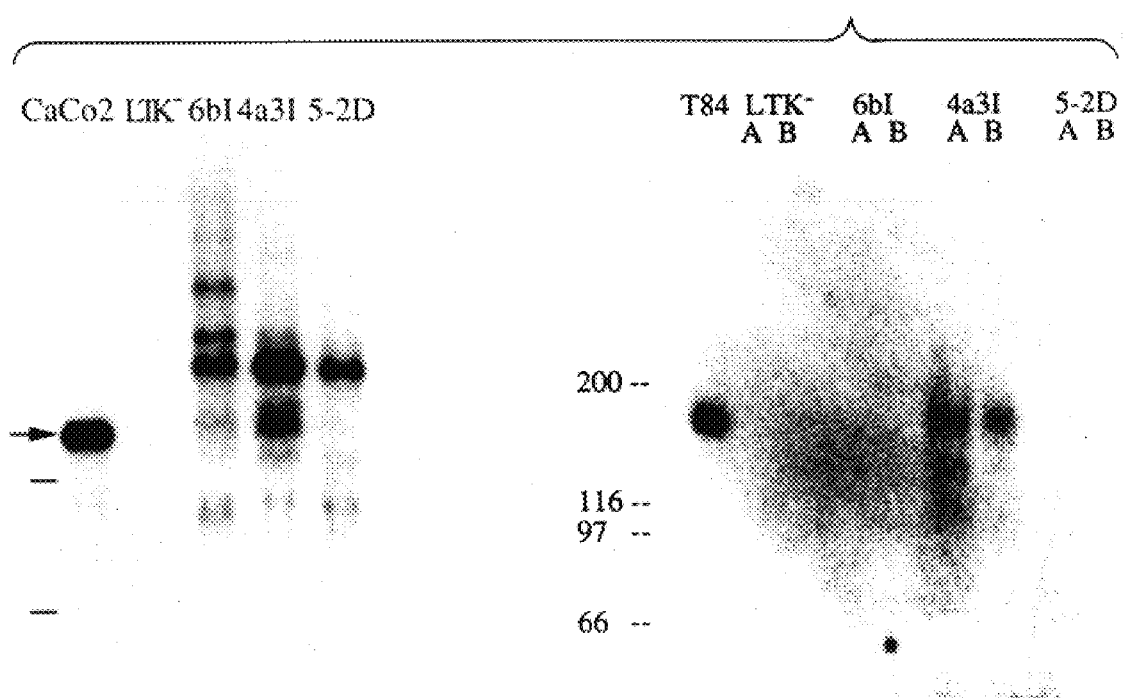

FIG. 13 is RNA and protein analysis of mouse L cell lines expressing human CFTR. (A) Total RNA from Caco2 (5 $\mu$g, lane 1), LTK$^-$ (10 $\mu$g, lane 2), 6B-I (10 $\mu$g, lane 3), 4a-3I (10 $\mu$g, lane 4), and 5-2D (10 $\mu$g, lane 5) cell lines were electrophoresed on a 1% formaldehyde/agarose gel, transferred to Hybond-N (Amersham), and hybridized with $^{32}$P-labelled cDNA probe. The autoradiogram is shown in the left panel. The 6.2-kb CFTR mRNA of the Caco2 cell line is indicated with the arrow. The parental LTK$^-$ lane does not show any signal as expected. The relative positions of the 28S and 18S rRNAs as indicated. (B) Protein fractions from nuclei and mitochondria (lanes A) and crude light membranes (lanes B) from the cell lines T84, LTK$^-$, 6B-I, 4a-3I and 5-2D are indicated. Bands were visualized by $^{125}$I-labelled rabbit anti-mouse antibody.

Figure 14:
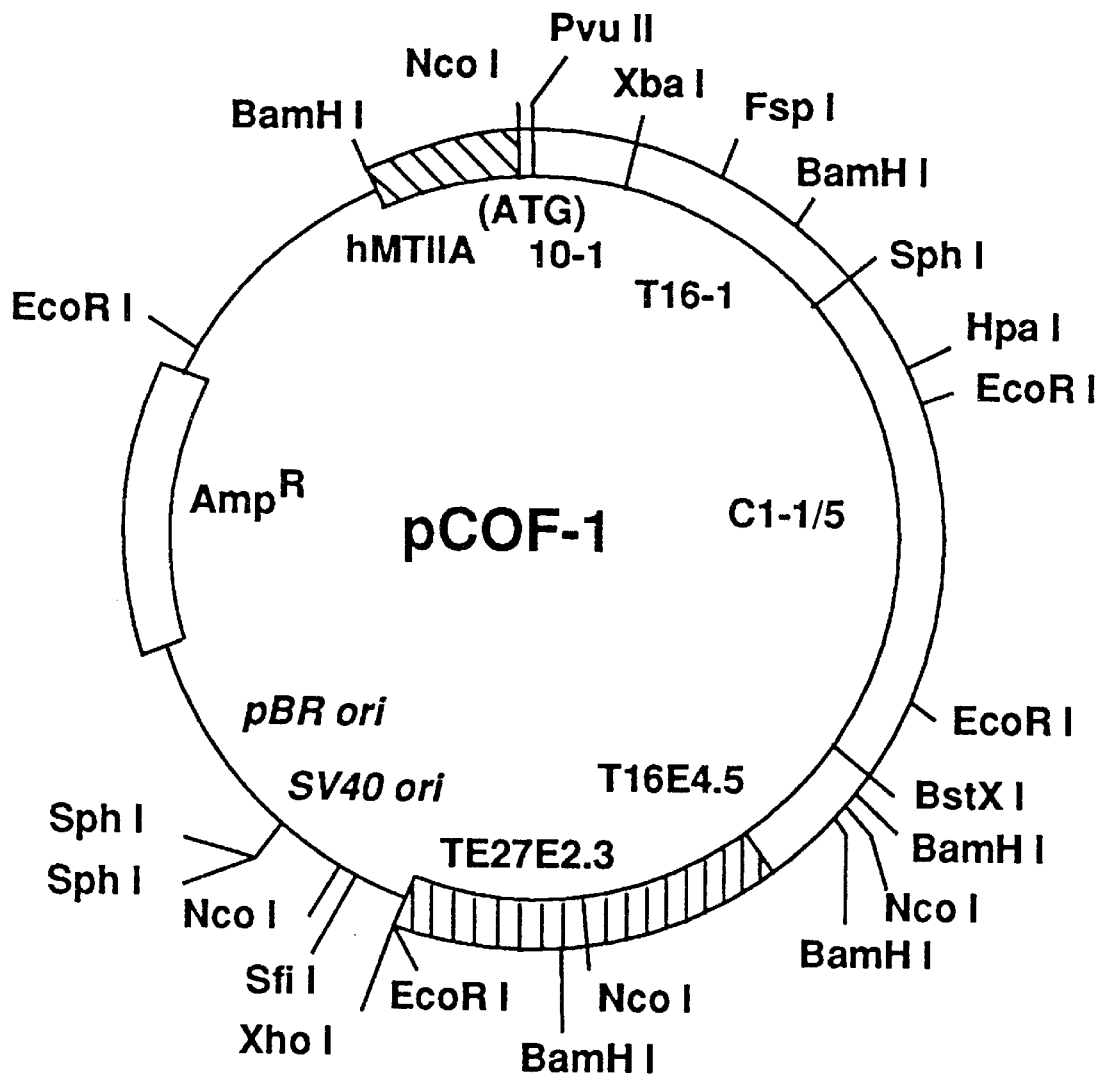

FIG. 14 is expression vector pCOF-1. The complete CFTR coding region (open boxes) is positioned downstream from the human metallothionein IIa (hMTIIa) promoter (hatched box). The human metallothionein IIa initiation codon is joined with that of CFTR at an Nco I site introduced by the synthetic oligonucleotides. 5'-CACTGC AGAC-CATGGAGAGGTCGCCTCTGGAAAAGGCCA GCGTT-3' and 5'-GACTGCAGCTGAAAAAAAGTTTGG AGACAACGCTGGCCTT-3'. The DNA sequence from exons 2 to 24 and its 3' flanking region was derived from clones 10-1 (Pvu II-Xba I), T16-1 (Xba I-Sph I), Cl-1/5 (Sph I-BstX1), T16E4.5 (BstXI-Nco I), and TE27E2.3 (Nco I-Xho I), as indicated. In pCOF$_A$F508, the 1-kilobase (kb) BamIII-HpI fragment was replaced with the corresponding fragment from clone Cl-1/5.

FIGS. 15A–15E are video microscopic detection of Cl$^-$ permeability in single L cells, SPQ fluorescence intensities (F) are expressed reltive to SPQ fluorescence intensity in the absence of Cl$^-$ quenching (F$_o$; the direction of changes in F$_o$/F reflect parallel changes in intracellular Cl$^-$ concentration. (A–C) Single cells, each indicated by a different symbol, are shown containing a frameshift construct leading to a predicted truncated CFTR (A); a mutant construct CFTR$\Delta$F508 (B); and an intact construct, CFTR (C). Forskolin (10 $\mu$M) and NO$^-_3$ medium were perfused over the cells for the periods indicated by solid bars. Time scale in C applies to A–C. (D) A single CFTR cell was repeatedly pulsed with NO$^-_3$ medium. Rate of fluorescence chage as well as peak response during constant pulses (1 min) was unchanged over the time course of exposure to forskolin, indicating that the cAMP-induced Cl$^-$ permeability is sustained. (E) Simultaneous determinations of Cl$^-$ concentrations (F$_o$/F) (open and solid squares) and cell volume, expressed as relative area of constant optical section (open and solid circles), in a single cell expressing CFTR (solid squares and circles)) and a single cell expressing truncated CFTR (open squares and circles). As indicated, the cells were exposed to 5 $\mu$M gramicidin and to 10 $\mu$M forskolin.

Figure 16A:
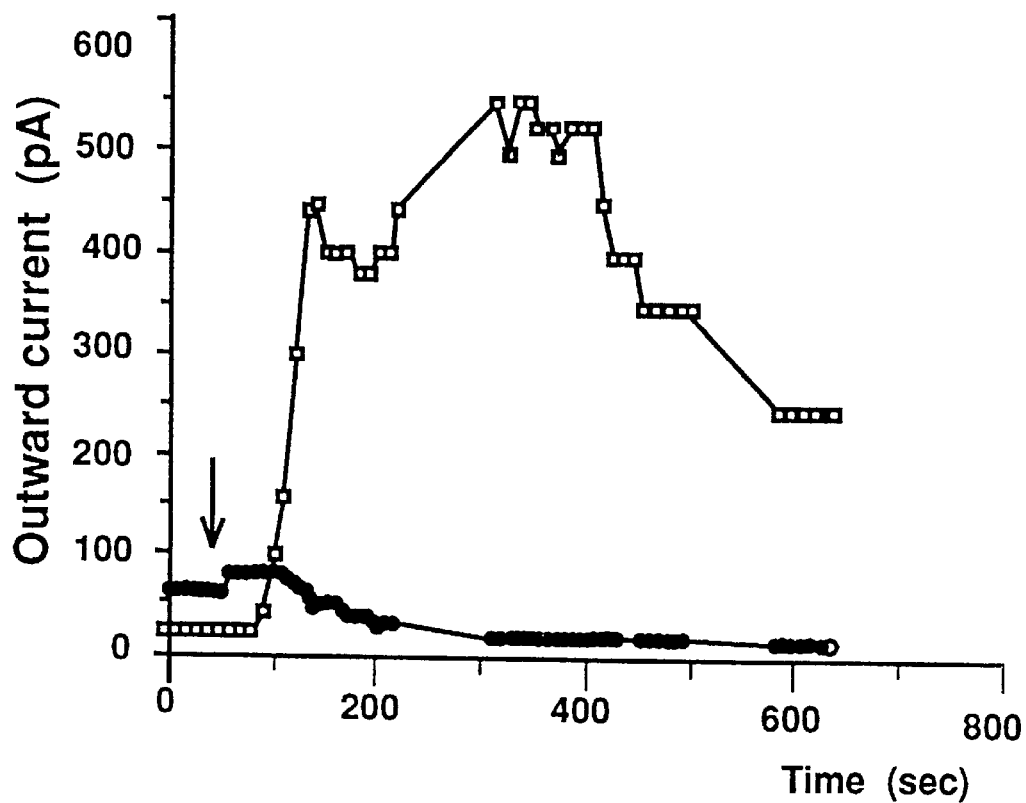
Figure 16B:
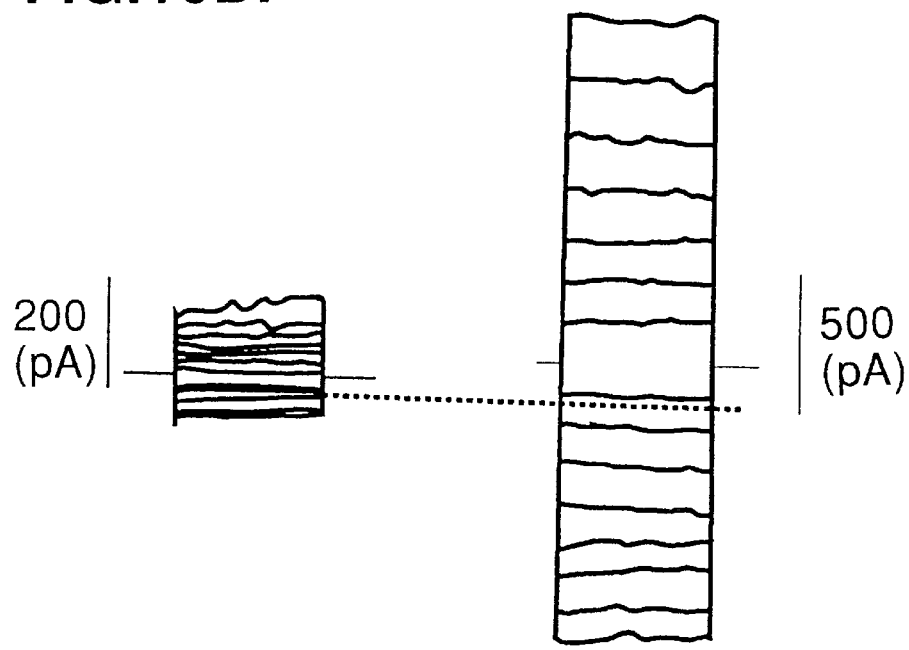
Figure 16C:
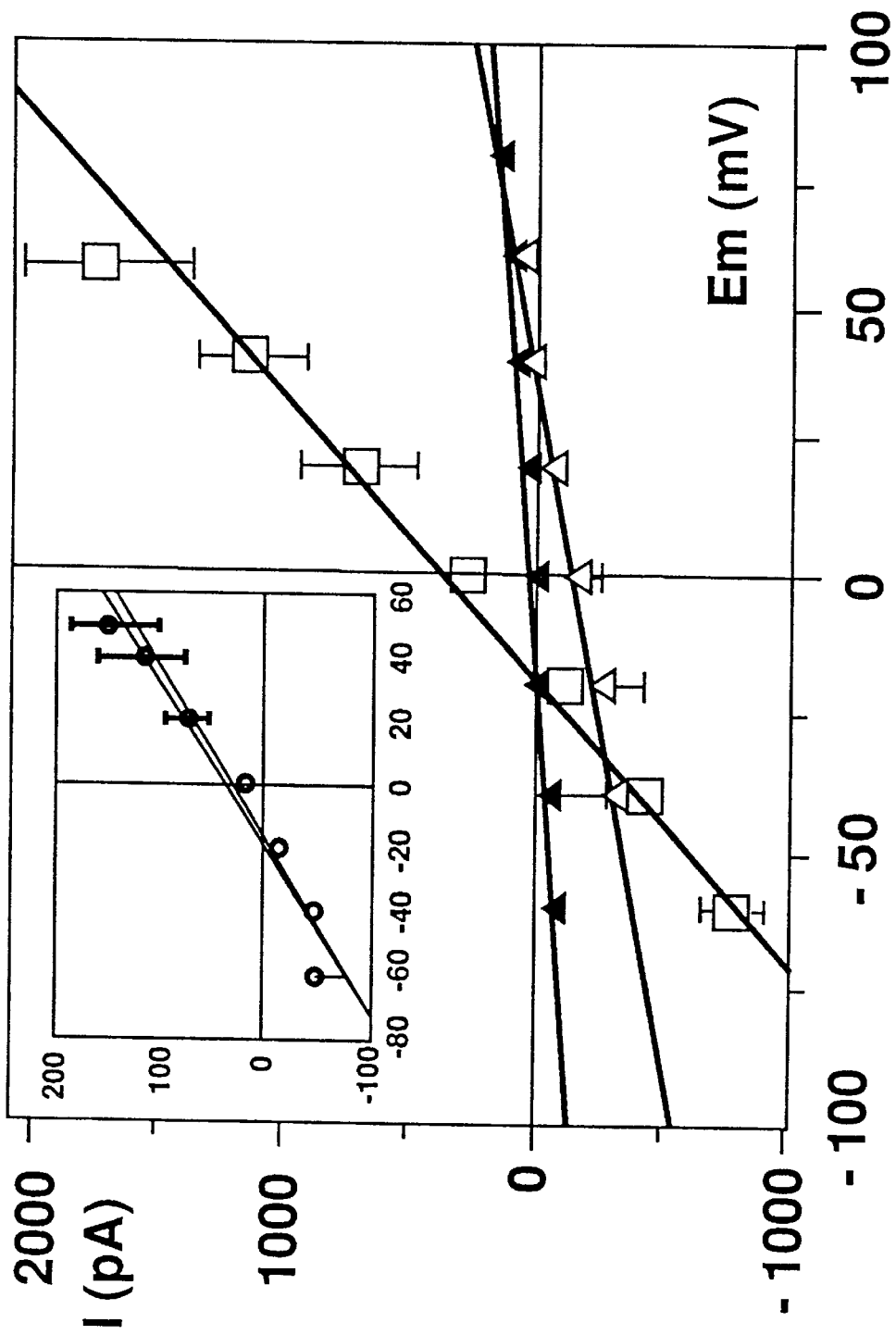

FIGS. 16A–16C are whole-cell Cl$^-$ currents in transfected L cell. (A) Time course of whole-cell currents measured from cells transfected with the frame-shift CFTR control construct (solid diamonds) and the intact CFTR construct (open squares) after the addition of a solution containing 10 $\mu$M forskolin, 1 mM isobutylmethylxanthine, and 100 $\mu$M N$^6$, O$^{2'}$-dibutylyladenosine 3',5'-cyclic monophosphate. The arrow indicates the time of solution addition. Outward currents were measured at E$_m$=+20 mV. (B) Whole cell current-voltage relationships for a CFTR-expressing cell before (Left) and 3 min after (Right) induced activation. The current scale for the nonstimulated cells is shown enlarged as indicated. The dashed line indicates the zero-current level. (C) Mean current-voltage relationships for CFTR cells (n=10) before and after activation (solid circles and open squares, respectively). Replacement of bath NaCl with sodium gluconate resulted in a shift in reversal protention of cAMP-activated currents (open triangle) (n=4).

DESCRIPTION OF THE PREFERRED EMBODIMENTS

The normal CFTR gene sequence and protein sequence is shown in FIG. 1. The sequence consists of cDNA identified and isolated from chromosome of mammalian cells in accordance with the procedure identified in co-applicants U.S. patent application Ser. No. 401,609, (abandoned), now U.S. continuation application Ser. No. 08/123,864 filed Sep. 20, 1993. It is believed that the cDNA of CFTR is made up of at least 27 exons as identified in applicant's pending Canadian patent application filed July 9, 1990.

The exact cause of the sequence instability is unknown, but the region frequently involved in this rearrangement is a 13 bp direct repeat in exon 6a of the CFTR gene as shown in FIG. 3. This region also shows sequence identity with consensus regulatory sequences in E. coli as noted in FIG. 3. It is possible that transcription initiates from this sequence, resulting in a product which is toxic to the bacterial host. It is also possible that the DNA sequence itself elicits an inhibitory response. In consequence, the transformation frequency and growth of the desired plasmid construct become extremely poor. The rearrangement of this sequence detected in the recovered plasmids may have alleviated its toxicity in bacteria. Thus, the inability to obtain a full-length CFTR cDNA in the original cloning experiment (Rommens et al, 1989) may also be explained.

Since most of the spontaneous sequence rearrangements detected disrupt the open reading frame of the full-length cDNA, none of the resulting clones are expected to be useful in functional complementation studies. Although it is possible to use alternative host/vector systems to overcome this problem, the convenience of the E. coli/pBR322-based cloning system required a better system.

The region of interest with respect to enhancing propagation of the cDNA in microorganisms and in particular in E. coli is in exon 6. A 13 base pair repeat has been found in exon 6. With reference to FIG. 1, the region of exon 6 is identified. More specifically, within exon 6 the repeat sequences occur at positions 923 through 935 and at 981 through 993. These repeat sequences are separated by approximately 44 base pairs.

It has been discovered that by modifying one or more of the base pairs in region 924 through 936 or 982 through 994 without changing the amino acid encoded by the respective codon results quite surprisingly in the propagation of the cDNA in a suitable microorganism, such as E. coli. The modified cDNA, in one of the repeat base pairs sections, does not produce a toxic effect in the microorganism so that a stable propagation of the cDNA can proceed. The benefit in the stable propagation of cDNA is not only from the standpoint of expression of the gene to produce the protein, but also for producing multiple copies of the cDNA for the CFTR gene to enable other uses of the gene, such as in drug and gene therapy for correcting the effects of CF.

Construction of Full Length cDNA

Two types of full length cDNA clones have been constructed to evaluate the modified cDNA. One of them is for efficient propagation in E. coli and the other one for expression in mammalian cells.

Figure 4:
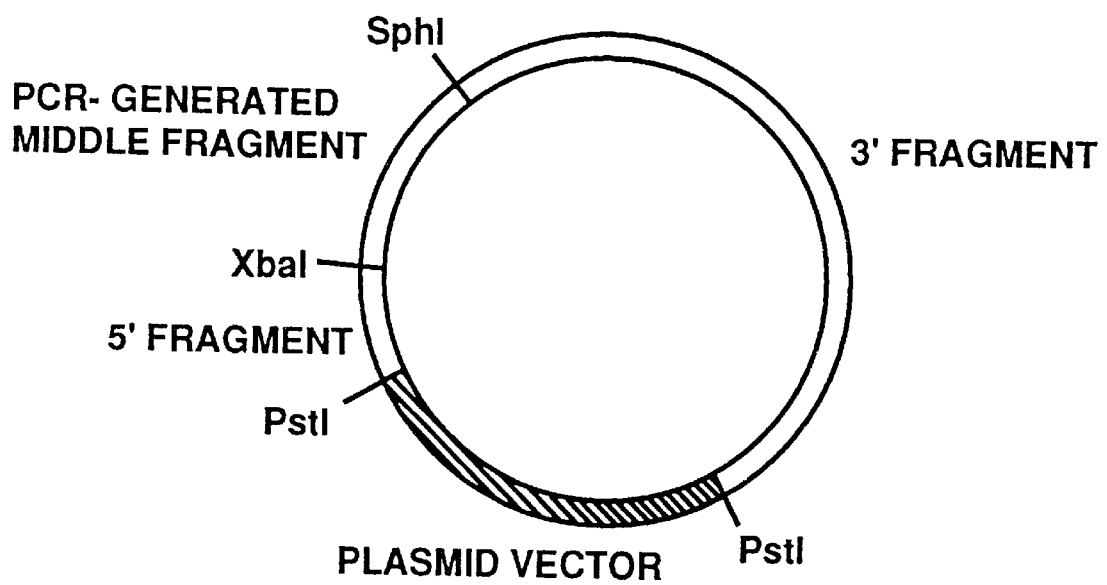
FIG. 4 is a schematic diagram showing the three components used in the construction of full-length CFTR cDNA.

Since the entire coding region of CFTR is present in multiple overlapping clones, it is necessary to construct the full-length cDNA in three separate steps. As shown in FIG. 4, there is the construction of the 5' end of the cDNA (from the beginning of the coding region to the XbaI site in exon 5), (Rommens et al, 1989); generation of the middle segment (from the XBaI site to the SphI site in exon 10) including the critical region by the polymerase chain reaction (PCR: Saiki et al, 1985); and (Riordan et al, 1989) construction of the 3' end of the cDNA from different existing clones (from SphI site to exon 24). The starting clones of this work have been described previously (Riordan et al, 1989).

To construct the 5' end of the cDNA in the mammalian expression vector, oligonucleotides were used to synthesize the open reading frame between the initiation codon and the end of exon 1 (the PvuII site). This fragment was inserted between the promotor of vector pSG3X and exon 2 of cDNA clone 10-1 (see FIG. 5). A single nucleotide modification (C to G) was introduced at the position immediately after the initiation codon to facilitate subsequent manipulation. The alteration also introduced an amino acid change from Glutamine to Glutamate.

Figure 6:
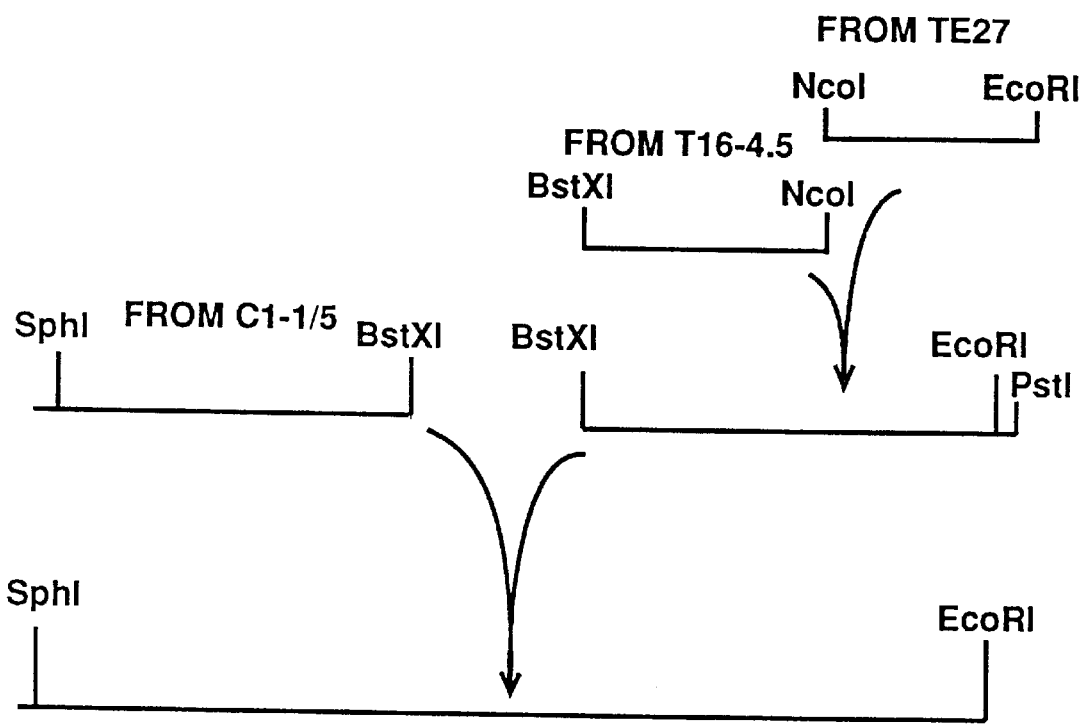
FIG. 6 is 3' end construction. The 3' coding region of the expression vector (pCOF-1) and pBQ6.2 was constructed in two sequential cloning steps. First, the 3' most portion, including the end of the coding sequence and the 3' untranslated region, was prepared by ligating a fragment from T16-4.5 (generated by BcoI partial digestion) to a fragment from the genomic clone TE27 (Rommens et al 1989). The resulting fragment was then joined with the SphI-BstXI fragment from Cl-1/5 (riordan et al 1989) at the BsXI restriction site to yield a 4 kb 3' end fragment.

To construct the 3' end of the cDNA, DNA fragments were obtained from three existing clones (FIG. 6): SphI to BstXI (exons 10–20) from Cl-1/5 (Riordan et al, 1989), BstXI to NcoI (exons 20–24) from T16-4.5 (Riordan et al, 1989), and NcoI to EcoRI (exon 24 to about 100 bp downstream from the polyadenylation signal) from TE27 (Rommens et al, 1989). The genomic DNA fragment included at the end of this construct to ensure proper transcription termination and mRNA processing. This 3' end construct was used for both the expression and propagation vectors.

Figure 7:
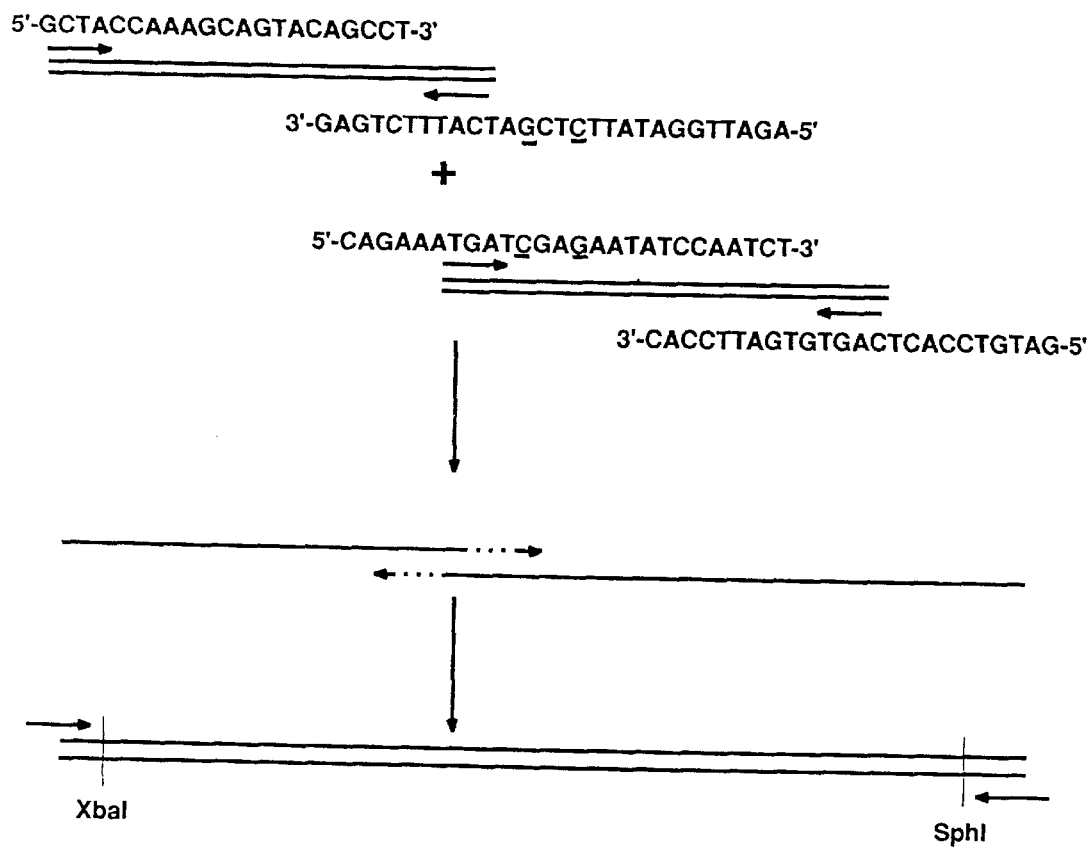
FIG. 7 is a schematic diagram showing the synthesis of the middle segment containing the modified sequence. Details are described herein.

The cDNA clone T16-1 (Riordan et al, 1989) was used as the template for generation of the middle segment, which was used for both vector systems. To introduce a sequence modification in one of the 13 bp repeat region of exon 6, the in vitro mutagenesis procedure based oligonucleotide-directed PCR (Higuchi et al, 1988; Ho et al, 1989) was used. Briefly, two overlapping segments, spanning exons 3 to 6 (536 bp) and exon 6 to 17 (867 bp), were generated from T16-1 by PCR with two sets of oligonucleosides (see FIG. 7). The two overlapping segments were joined by the PCR procedure with the outermost, flanking oligonucleotide primers. The product, 1.38 kb in size, was then digested with XbaI and SphI to generate the modified middle segment.

Figure 8:
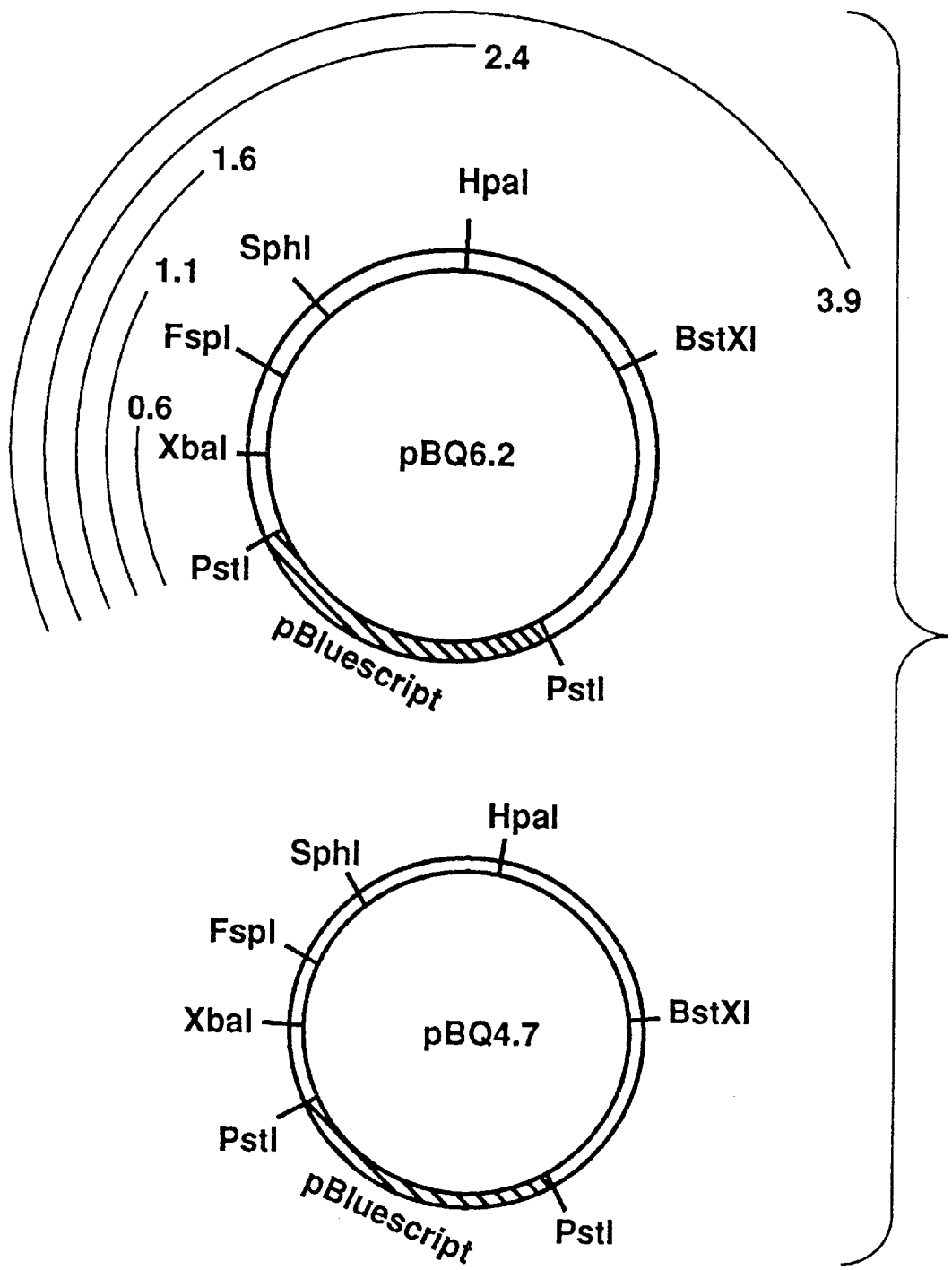
FIG. 8 is propagation vectors pBQ4.7 and pBQ6.2. The construction of these plasmids is provided in description of the invention. Key restriction sites are marked. The sizes of the transcripts generated by the T7 RNA polymerase (from the PstI site to each of the marked restriction sites ) are also indicated (in kilobases).

The pBluescript® vector from Stratagene was used as the basis propagation vector. The 5' end of the full-length cDNA in this vector was derived from cDNA clone 10-1 (between the PstI and XbaI sites). The resulting clones were named pBQ4.7 and pBQ6.2 (FIG. 8).

Figure 5:
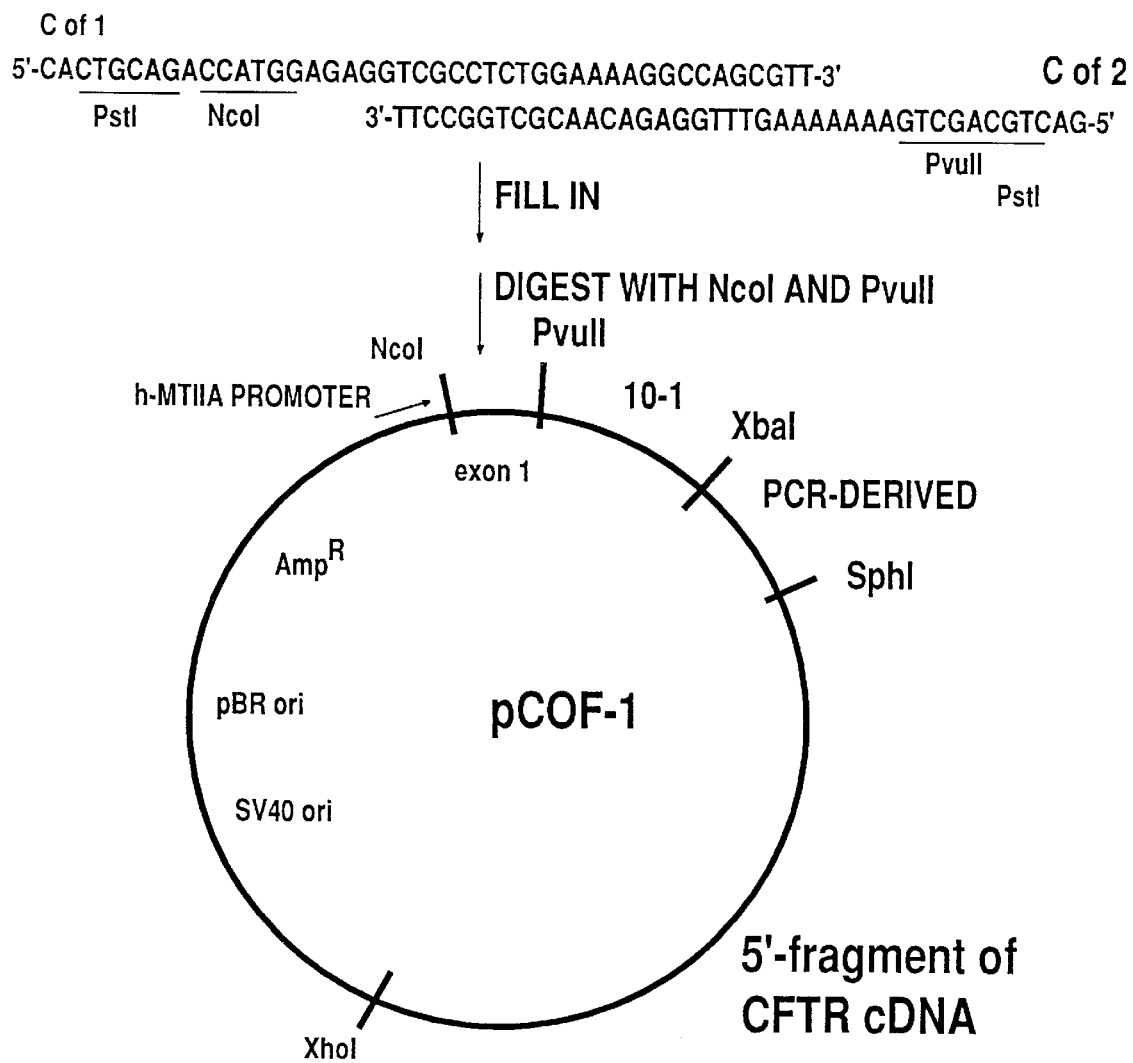
FIG. 5 is the generation of the 5' end of CFTR cDNA for the expression vector pCOF-1. Two overlapping, oppositely oriented oligonucleotides, Cof1 (44-mer) and Cof2 (40-mer), were used in the generation of the exon 1 sequence. A double stranded molecule was synthesized from these two oligonucleotides with the Klenow fragment of DNA polymerase. An NcoI site was introduced at the initiation codon to facilitate subsequent cloning. The PCR-generated fragment was digested with NcoI and PvuII and ligated to the remaining portions of the CFTR cDNA, including the PvuII to XbaI fragment of cDNA clone 10-1, the PCR-modified middle fragment and the 3' fragment. The procedures used to generate the two latter segments are described with reference to FIGS. 6 and 7. The position of the human metallothionein IIA promoter, the bacterial ampicillin-resistance gene, the pBR origin of replication and the SV40 origin of replication are marked.

The plasmid pSGM3X was used as the basic mammalian expression vector. It is similar to p SGM1 previously reported by Meakin et al (1987), except that the human metallothionein promoter was inserted in an opposite orientation and that a XhoI site was inserted in the KpnI site within the Ecogpt gene. The resulting expression vector was named pCOF-1 (FIG. 5).

Sequence Verification

Since errors are often introduced into PCR products due to infidelity of the Taq polymerase, the middle segment of the cDNA clones were first verified by DNA sequencing. The procedure of dideoxy termination was used according to the US Biochemical Sequenase® kit. Consequently, it was necessary to replace a small segment (the XbaI site in exon 6 to the FspI site in exon 7) of the clone with the corresponding segment from T1601. Overlapping DNA sequencing was then performed for the entire open reading frame of each of the completed full-length cDNA constructs.

In Vitro Translation

To produce large quantities of RNA from the propagation vector (pBQ4.7 and pBQ6.2) for the purpose of in vitro translation, the mCAP® mRNA capping kit from Stratagene was used.

Since the open reading frame predicts a protein of 170, 999 kilodaltons (kd), it would be difficult to produce a product of this size in vitro. It was therefore necessary to use differently prepared templates to examine various segments of the open reading frame. To prepare these templates, the propagation vector pBQ6.2) was digested with FspI, EcoRI, HpaI and XhoI, accordingly.

in vitro translation was performed with a rabbit reticulocyte lysate kit from Promega Corporation and $^{14}$C-labelled leucine from Amersham.

Transfection Studies in Mouse LTK Cells

The calcium phosphate co-precipitation procedure for introduction of plasmid DNA into mouse LTK-cells has been described previously (Meakin et al, 1987). The plasmid pSTK7 was used for cotransfection with the expression vector pCOF-1. As a control vector, a plasmid construct similar to pCOF-1, except for the deletion of a single base pair in exon 1 was used; this deletion was expected to result in premature termination of translation.

The mouse LTK-cells were passaged in α-MEM medium supplemented with glutamine, 10% fetal bovine serum and antibiotics. Biochemical selection for TK positive cells was achieved in medium containing hypoxanthine, aminopterin and thymidine (HAT medium).

DNA and RNA Analyses

Plasmid and DNA samples were prepared from the bacterial cells and genomic DNA from transfected mouse L cells. Total RNA was extracted from mammalian cells for examination of gene expression. Standard procedures, essentially as described by Sambrook et al (1989), for DNA and RNA analyses were used.

Protein Analysis

Animal cells were harvested in TEN buffer (40 mM Tris-HCl, pH 7.5, 1 mM EDTA, 150 mM), after the cells were washed in phosphate-buffered saline. Cells were collected by scraping, resuspended in 2560 mM Tris-HCl (pH 8), and stored in −80° C. ready for total protein extraction. For SDS-polyacrylamide gel electrophoresis, the frozen cells were resuspended in the loading buffer and boiled for 5 min prior to electrophoresis according to the procedure of Laemmli et al (1970).

Transfer of protein from polyacrylamide gel to nitrocellulose was performed overnight at 0.4 mA according to the procedure of Towbin et al (1979). The membrane was baked at 80° C. for 90 min. Detection of CFTR was accomplished with the use of a monoclonal antibody (gift of N. Kartner and J. Riordan) prepared against a portion of the predicted protein (amino acid residues 347–698) and the ProtoBlot® AP System according to procedures recommended by the supplier (Promega Corporation) with 1% BAS as a blocking agent.

Vector Construction

Three plasmid constructs were made in this study—pBQ4.7; pBQ6.2 and pCOF-1 as described in the previous section. pBQ4.7 is a full-length cDNA clone contained in the Bluescript® vector; it contains the entire coding region except the 3' untranslated region. pBQ6.2 contains the same sequence as in pBQ4.7 plus the 3' untranslated region. Both of these plasmids contain modification in the first 13 bp direct repeat in exon 6b (FIG. 3). The full-length cDNA construct in pCOF-1 is inserted downstream from the human metallothionein IIA promoter in the vector pSGM3X and the coding region is flanked by CFTR genomic DNA sequence at the 3' end. In addition to the modification introduced into the exon 6b region of the cDNA, as in the two previous constructs, pCOF-1 has another modification (C to G) in the first nucleotide after the presumptive initiation (ATG) codon in exon 1.

As the first step in examining their integrity, restriction enzyme digestions were used to derive a map for each of these full-length cDNA constructs. The results showed that all of them produced a set of DNA fragments as expected. It is, however, of interest to note that there was one DNA fragment in each of the digestions which appeared to have a different mobility when compared to the pattern of the corresponding parental cDNA clones displayed on polyacrylamide gel. The mapping data located the fragments with the altered mobility to those containing the 13 bp direct repeats.

Figures 9, 10:
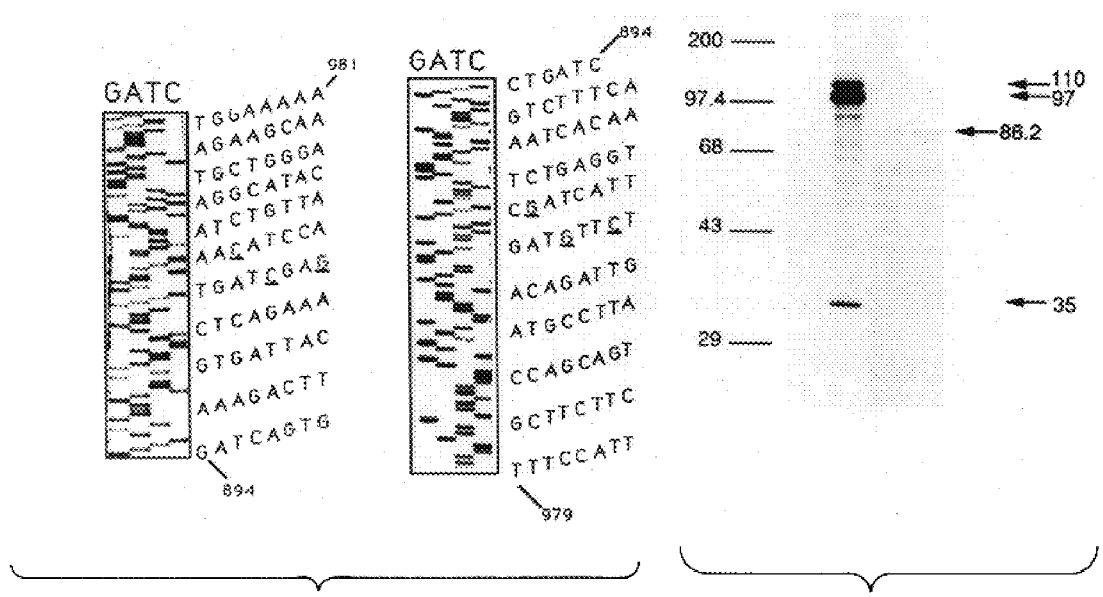
FIG. 9 is DNA sequencing ladder showing the modified sequence in exon 6b. The sequencing reaction was performed with the use of an oligonucleotide primer (19-mer) corresponding to a sequence in exon 6a starting at nucleotide 771 (5'-GCTAATCTGGGAGTTGTT-3'). The altered nucleotide in the sequence are underlined.
FIG. 10 is in vitro translation of CFTR. The products from in vitro translation reactions were separated on a 10% polyacrylamide -SDS gel. The gel was stained by Coomassie Blue after electrophoresis; it was then soaked in Enhance® (New England Nuclear) and dried at 60° C. under vacuum before exposure to X-Omat film (Kodak). Lane 1: no added RNA, lane 2: protein translated from the Brome Mosaic Virus RNA (BMV) (as size and reaction conditions control); lanes 3 and 4: duplicate samples of capped mRNA prepared by T7 RNA polymerase on template pBQ6.2 digested with HpaI. The positions for the protein molecular weight standards (purchased from BRL Labs) are indicated on the left in kilodaltons. The expected product of 82.6 kb (from the RNA generated from the pBQ6.2 plasmid) is marked. Also marked (by arrows) are the sizes of the BMC protein products, shown in lane 2.

To ensure the DNA sequence was intact as designed, the middle segment containing the modified segment was examined by DNA sequencing. The result showed that 3 bp were altered in the region. While two of the modifications (T to C at position 930 and A to G at 933) were inserted as expected, an additional change (T to C at position 936) was found (FIG. 9). This unanticipated alteration was found in all five clones examined, suggesting that it was introduced by an error in the synthesis of the oligonucleotide primer. Nevertheless, this error was located outside of the "−35" prokaryotic consensus sequence (Hawley and McClure 1983) and did not alter the encoded amino acid (FIG. 3).

Two other undesired nucleotide changes were detected in the middle cDNA segment. Since these latter substitutions, probably introduced during PCR, would change the encoded amino acids, it was necessary to replace the region containing these changes with a segment from the original plasmid.

The DNA sequence in all three resulting clones appeared to be stable after long term propagation in $E.\ coli$. Their entire coding region was sequenced and no additional changes were detected. It was noted that the transformation efficiency of these constructs in bacteria increased substantially (100 times higher than the unmodified cDNA) and that the copy number of plasmids (as reflected by the yield in DNA preparation) also increased.

Protein Synthesis by in Vitro Translation

To ensure that the open reading in the full-length cDNA was uninterrupted, the in vitro translation method was performed. Accordingly, the propagation vector was linearized at an appropriate restriction site in the circular plasmid and used as the template for production of RNA suitable for translation in vitro. Since the entire CFTR protein would be probably too large to be translated in vitro, the experiment also included shorter transcripts produced from templates interrupted within the coding region.

An example of the result is shown in FIG. 10. The template used for this experiment was pBQ6.2 linearized at the HpaI site; the in vitro translation product was expected to be 86.2 kd. As shown in FIG. 10, a band migrating at the position of the expected molecular weight is clearly visible, indicating that translation initiates at the ATG codon as predicted and continues through the HpaI site in exon 13. The identity of this protein is also confirmed by its ability to react with a monoclonal antibody against CFTR. The other, smaller proteins observed in the products are probably results of premature termination or intenal initiation of translation.

Similar experiments were performed with the plasmid treated with XbaI and EcoRI. Protein bands corresponding to the expected translation products 19 and 77.5 kd, respectively, were readily detectable on the polyacrylamide gel. These results, therefore, provided further confirmation that the predicted open reading frame was correct and intact in the full-length cDNA constructs.

Expression in Mouse L Cells

To examine if CFTR could be produced in heterologous mammalian cells, the pCOF-1 plasmid was used to transfect mouse LTK-cells. Another plasmid containing the herpes simplex virus TK gene was included in the transfection to allow biochemical selection of cells that were successfully transfected. A plasmid (pCONZ) which suffered a single base pair deletion immediately adjacent to the 3' initiation codon was used in a parallel transfection experiment as a negative control (as the frameshift would result in no CFTR products).

DNA Analysis

HAT-resistant L cell colonies were isolated and expanded into individual mass cultures and genomic DNA were isolated from these cultures for characterization of integrated plasmid DNA. As expected, all of the HAT-resistant L cell lines was found to contain an intact HSV TK gene (as demonstrated by gel-blot hybridization analysis). In addition, the copy number for the integrated plasmid DNA was found to vary among different lines, an anticipated from the calcium phosphate co-precipitation protocol. Gel-blot hybridization analysis was then performed for the cell cultures transfected with pCOF-1 and pCONZ. The full-length cDNA clone (a 6.2 kb PstI fragment from pBQ6.2) was used as proof to examine the CFTR sequence.

Figure 11:
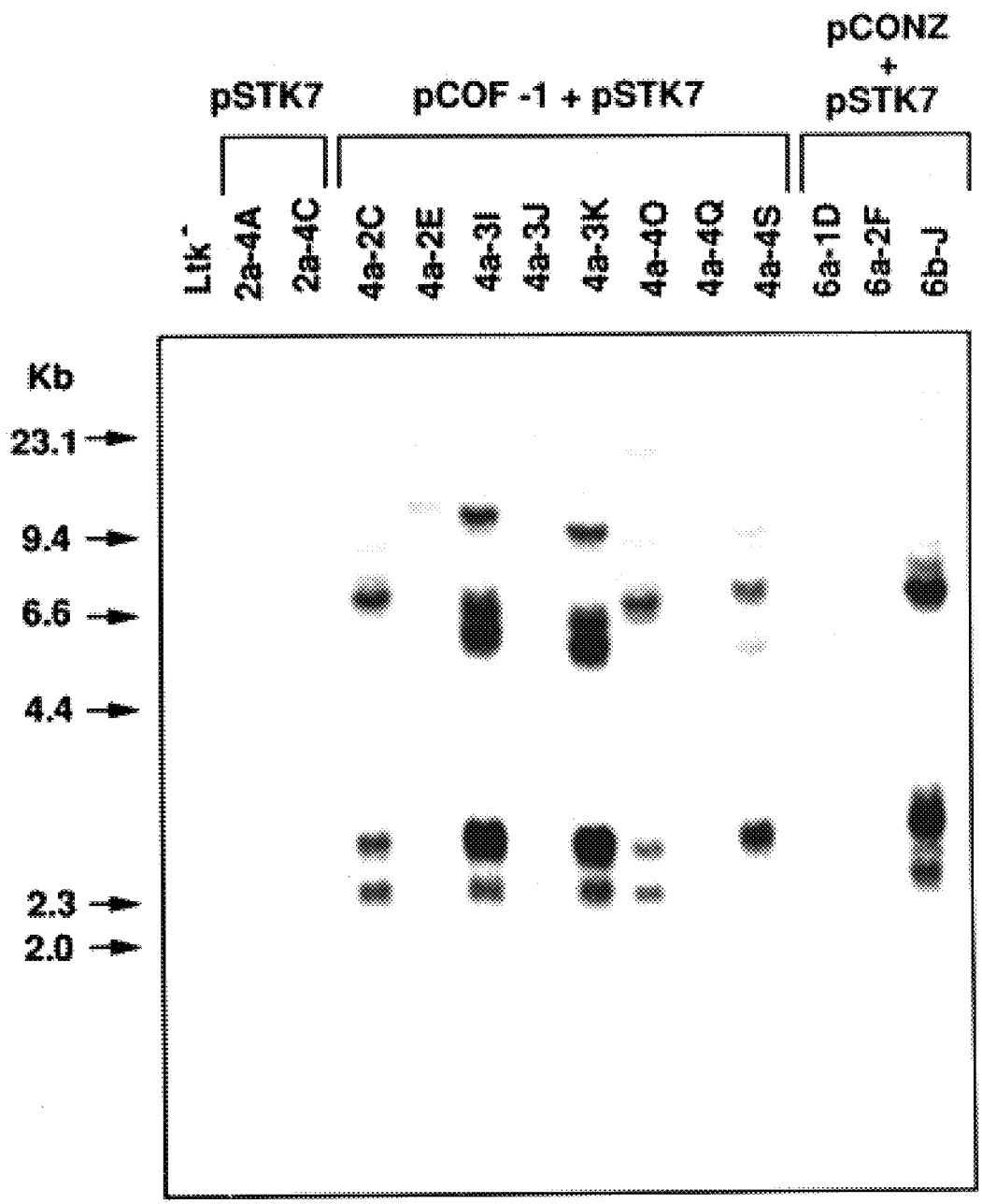
FIG. 11 is DNA hybridization analysis of integrated plasmids. Genomic DNA samples were prepared from each cell line, digested with BamHI and separated on a 0.7% agarose gel in Tris-acetate buffer. The restricted DNA was then transferred to Zetabind (Bio-Rad Labs) membrane.

Among the 15 pCOF-1/pSTK7 co-transfected cell lines, 14 were found to contain at least a portion of the CFTR cDNA, as judged by the hybridization pattern of EcoRI-digested DNA from these lines. Five of these lines shows a 1.5 kb and 2.5 kb band, as predicated for an intact cDNA. For the remaining lines, the size of the EcoRI fragment was different from those predicted, indicating rearrangement or integration occurred through this region of the cDNA. Upon further analysis with BamHI and NcoI digestion, however, only four of the five lines showed intact 5' and 3' ends of the cDNA (see FIG. 11). The apparently intact clones were 4a-2C, 4a-3I, 4a-3K, and 4a-4S.

Similar DNA analysis was performed for cell lines co-transfected with pCONZ and pSTK7. Among the 10 clones examined, nine appeared to contain CFTR sequence and eight of them showed the predicted 1.5 kb and 2.5 kb EcorI fragments (see FIG. 12). Further analysis with BamHI and NcoI on five of them revealed that four (6a-1D; 6a-2F; 6b-J and 6b-K) contained intact 5' and 3' ends.

RNA Analysis

Expression of CFTR in the transformed mouse cell lines was next examined by RNA blot hybridization analysis. Two of the pCOF-1 transfected lines (4a-3I and 4a-3K) were found to express high levels of RNA (see FIG. 12a) but the remaining two lines 4a-1C and 4a-4Q) were low. In addition to the 6.2 kb band expected for correctly initiated and terminated CFTR RNA in these lines; however, hybridizing sequences were also detected at the 9–10 kb range, suggesting improper initiation or termination. A similar, high expression pattern was observed for three of the lines transfected with pCONZ (6a-1A; 6a-1D and 6b-J) (FIG. 12a). For clone 6a-2F, only a low level of the 6.2 kb species was detected. No RNA could be found for clone 6b-K, despite the presence of an apparent intact CFTR sequence.

The level of CFTR-derived RNA present varied among the cell lines mentioned above, with the strongest signals seen in clones 4a-3I and 6b-J. The variation was not due to poor sample preparation, as confirmed by hybridization analysis of the same blot with the TK probe (FIG. 12B).

Protein Analysis

Protein was then extracted from several representative cell lines and examined for the presence of CFTR-related products.

In the right panel of FIG. 13, a 170 kd band of appropriate size for the CFTR protein was clearly observed in the light membrane fraction, B, of 4a-3I. No CFTR protein was detected in LTK⁻ extracts or in the 6b-I extracts.

1) A single 170 kdalton band was observed in the light membrane fraction from the cell line 4a-3I. This cell had been demonstrated by DNA analysis to contain multiple copies of the intact promoter of the expression vector and of the CFTR gene. RNA analysis also indicated expression of high levels of mRNA for this clone.

2) In contrast, the cell line 6b-I, generated with the mutant gene does not express a reacting 170 kdalton band. This line generated by co-transfection with the pCONZ plasmid was shown to have an intact promoter and gene portion. In addition, high levels of RNA were detected. Identical results for these samples were obtained even when the extracts were not subjected to heating prior to gel loading.

3) 170 kdalton bands were not observed in the cell line 4a-2D generated by the transfection experiment with the pCOF-1 plasmid and the cell line 2a-4A generated by the transfection with the pTK7 plasmid only. Genomic DNA analysis of the cell line 4a-2D indicated that only portions of the CFTR gene had been incorporated. As expected, no CFTR RNA could be detected.

For comparison, also shown on the protein analysis in FIG. 13 is a crude membrane preparation of the cell line T84 (provided by N. Kartner and J. Riordan). A single diffuse band is observed in the T84 preparation that is of comparable size of that expressed in the 4a-3I cell line. In conclusion, the cell line 4a-3I appears to be producing a 170 kdalton CFTR protein as expected from the open reading frame of the pCOF-1 plasmid A CAMP-inducible chloride permeability has been detected in mouse fibroblast (L cell) lines upon stable integration of a full-length cDNA encoding the human cystic fibrosis transmembrane conductance regulator (CFTR). As indicated by a Cl⁻-indicator dye, the Cl⁻ permeability of the plasma membrane increases by 10- to 30-fold within 2 min after treatment of the cells with forskolin, an activator of adenylyl cyclase. The properties of the conductance are similar to those described in secretory epithelial cells; the whole-cell current-voltage relationship is linear and there is no evidence of voltage-dependent inactivation or activation. In contrast, this cAMP-dependent Cl⁻ flux is undetectable in the untransected cells or cells harboring defective cDNA constructs, including one with a phenylalanine deletion at amino acid position 508 ($\Delta$F508), the most common mutation causing cystic fibrosis. These observations are consistent with the hypothesis that the CFTR is a cAMP dependent Cl⁻ channel. The availability of a heterologous (nonepithelial) cell type expressing the CFTR offers an excellent system to understand the basic mechanisms underlying this CFTR-associated ion permeability and to study the structure and function of the CFTR.

We describe the construction and use of a mammalian expression vector to produce human CFTR in a long-term mouse fibroblast culture. We show that expression of CFTR induces a cAMP-dependent Cl⁻ conductance, which is normally not observed in these cells. This expression system is suitable for study of the Cl⁻ conductance pathway and its regulation and to provide medical treatment for CF.

Plasmid Vectors

The mammalian expression vector pCOF-1 is a derivative of pSGM3X, which is similar to pSMG1 (Meakin et al, 1987), except that the human metallothionein IIa promoter (Karin et al, 1982) was inserted in the opposite orientation and a Xho I site was inserted in the Kpn I site within the Ecogpt gene. To reconstruct the full-length CFTR cDNA in pCOF-1 (FIG. 14), the bulk of the coding region (exons 2–24) was obtained from partial cDNA clones (Riordan et al, 1989), except that the three silent nucleotide substitutions (T→C at position 930, A→G at position 933, and T→C at position 936) were introduced into the exon 6b region with oligonucleotide-mediated mutagenesis by the polymerase chain reaction (19, 20). The 3' untranslated region of CFTR in pCOF-1 was derived from the genomic DNA clone TE27E2.3 (Rommens et al, 1989). The entire coding region of exon 1 (from the initiation codon to the Pvu II site) was generated by two complementary synthetic oligonucleotides and the Klenow fragment of DNA polymerase I, where a single nucleotide substitution (C→G) was introduced immediately after the initiation codon (underlined in the legend to FIG. 14) to create a Nco I site for ligation to the human metallothionein IIa promoter. The latter substitution changed the encoded amino acid glutamine to glutamic acid. The construction of control plasmid pCONZ was similar to that of pCOF-1, except that a single nucleotide was deleted 35 base pairs downstream from the initiation codon. A truncated protein would be predicted from this frameshift construct. The plasmid pCOFΔF508 was generated by replacing sequences of exons 9–13 in pCOF-1 with the corresponding fragment from Cl-1/5, a cDNA containing the ΔF508 mutation. The full-length cDNA clone pBQ6.2 contained a 6.2 kb Pst I fragment in pBluescript (Stratagene) and was constructed similarly to pCOF-1 except that the exon 1 region was derived from clone 10-1. The integrity of the CFTR cDNA inserts in pBQ6.2, pCOF-1, and the critical regions in the other plasmid constructs were verified by DNA sequencing. The plasmid vector (pSTK7) containing the herpes simplex virus thymidine kinase gene, used in the cotransfection experiments, has been described (Meakin et al). Bacterial cell cultures and plasmid DNA samples were prepared according to standard procedures (Sambrook et al, 1989).

Cell Culture and DNA Transfection

Each of the three test plasmids (20 μg), pCOF-1, pCONZ, and pCOFΔF508, was cotransfected with pSTK7 (1 μg) into mouse LTK⁻ cells by calcium phosphate coprecipitation (Meakin et al). Biochemical selection for thymidine kinase-positive cell was achieved in minimal essential medium supplemented with hypoxanthine/aminopterin/thymidine (HAT; gibco/brl). In some experiments, the test plasmids were linearized at the unique Sfi I site (FIG. 14). High molecular weight DNA was isolated from each clonal cell line (Miller et al, 1988), digested with restriction enzymes EcoRI, BamHI, and Nco I, and analyzed by agarose-gel-blot hybridization (Sambrook et al, 1989) with the full-length cDNA (insert from pBQ6.2) as probe. Total RNA was extracted (MacDonald et al, 1987) and analyzed by agarose-gel-blot hybridization (Sambrook et al, 1989).

Protein Analysis

Cells were homogenized in a hypotonic buffer containing 10 mM KCl, 1.5 mM MgCl$_2$, and 10 mM Tris.HCl (pH 7.4). Nucleic and mitochodria were collected by centrifugation at 4000×g for 5 min (fraction A). A crude membrane fraction was then collected by centrifugation at 9000×g for 15 min (fraction B). Membrane pellets were dissolved in loading buffer and separated on a NaDodSO$_4$/polyacrylamide (6%) gel (Laemmli, 1970). Proteins were transferred to nitrocellulose as described (Towbin et al, 1979) and immunodetected with monoclonal antibody M3A7 (Kartner et al, 1991).

6-Methoxy-1-(3-sulfonatopropyl)quinolinium (SPQ) Fluorescence Assay

L cells grown on glass coverslips for 1–2 days were uniformly loaded with the Cl⁻-indicator dye SPQ by incubation in hypotonic (1:2 dilution) medium containing 20 mM SPQ at room temperature for 4 min. The mounted coverslip was perfused continuously at room temperature with medium containing 138 mM NaCl, 2.4 mM K$_2$HPO$_4$, 0.8 mM KH$_2$PO$_4$, 10 mM Hepes, 1 MM CaCl$_2$, 10 mM glucose, and 10 μM bumetanide (pH 7.4) on the stage of an inverted microscope. NO⁻$_3$ medium was identical except that NO⁻$_3$ replaces all but 10 mM Cl⁻. To minimize Cl⁻ fluxes through nonconductive pathways, we performed the experiments in the absence of HCO⁻$_3$ and in the presence of bumetanine, inhibiting the anion exchanger and Cl⁻/cation cotransporters, respectively. Fluorescence and the differential interference contrast imagine were performed simultaneously (25–27). SPQ fluorescence intensities (F) were normalized to total SPQ fluorescence F$_o$, determined as F measured in the absence of intracellular Cl⁻, since autofluorescence was negligible, Calibration (n=7 cells) were performed essentially as described (Foskett, 1990). The effective quenching constant $K_{Cl}$ was 15 M⁻¹; the testing intracellular Cl⁻ concentration was ≈70 mM. Cell volume changes were obtained by planimetry of differential interference contrast images (26, 27) and are presented as relative changes in the areas of the measured optical sections. By exposure of the cells to media of various osmolarities, we observed that differential interference contrast imaging of a single optical section can detect volume changes.

Whole-Cell Current Recordings

Membrane currents were measured at room temperature 12–24 hr after plating cells with whole-cell patch-clamp techniques (Hamill et al, 1981). The patch pipet contained 110 mM sodium gluconate, 25 mM NaCl, 8 mM MgCl$_2$, 10 mM hepes, 4 mM Na$_2$ATP, and 5 mM Na$_2$EGTA (pH 7.2). The bath contained 135 mM NaCl, 2.4 mM K$_2$HPO$_4$, 0.8 mM DH$_2$PO$_4$, 3 mM MgCl$_2$, 1 mM CaCl$_2$, 10 mM Hepes, and 10 mM glucose (pH 7.2). To examine the time course of a cAMP-evoked conductance changes, membrane potentials were alternately clamped at −30 and +20 mV for 600 and 400 ms, respectively. Current-voltage relationships were determined by measuring the currents at the end of 400-ms voltage steps from 0 mV to +70 mV (10 mV increments). Cell capacitance was compensated using cancellation circuitry of the EPC7 patch-clamp amplifier.

DNA Transfection

Stable mouse fibroblast cell lines containing full-length CFTR or mutant cDNA, as well as cell lines with the pSTK7 plasmid alone, were established. Four cell lines with pCOF-1 (4a-2C, 4a-3I, 4a-3K, and 4a-S) contained an intact human metallothionein IIa promoter and the CFTR coding region, as judged by DNA analysis (data not shown). Similarly, four cell lines (6a-1D, 6a-2F, 6b-I, and 6b-K) for pCONZ control cDNA with the frame-shift mutation three for pCOFΔF508 (5-2C, 5-1A, and 5-2D) cDNA with the major CF mutation and two for pSTK7 (2a-4A and 2a-3C) were identified).

RNA Analysis

Abundant levels of RNA transcripts of ≈10 kb in size were detected in cDNA transected cells FIG. 13, left panel. Although their size was larger than the anticipated 6.2 kb, the result appeared to be consistent among all cell lines. It seemed probable that an alternative polyadenylylation site (s) instead of those contained in the cDNA constructs were utilized. Thymidine kinase-specific transcripts were detected in all HAT-resistant cell lines tested.

Protein Analysis

Cells expressing CFTR mRNA (as represented by the cell line 4a-3I) contained an antibody-reacting protein band that was indistinguishable from mature CFTR expressed endogenously in membranes of the colonic carcinoma cell line T84 (FIG. 13B, right panel). The amount of protein was within the range of that observed for T-84 cells, with a significant portion in the light membrane fraction. Reacting bands were not detected in untransfected LTK$^-$ cells or in cell transfected with CFTR gene predicted to produce a truncated product (line 6B-I). The latter result was expected as the antibody was directed against the C terminus of the protein. No immunoreactive material was observed for CFTRΔF508 in the examined fractions (line 5-2D) (Cheng et al, 1990). It was therefore uncertain if the mutated protein was produced in these transfected cells.

SPQ Fluorescence Assay

To investigate if expression of CFTR affected Cl$^-$ conductance, a single-cell assay based on quantitative fluorescence intensity measurements of the Cl$^-$ indicator dye SPQ was performed. The basic protocol involved exposing cells to NO$^-_3$ medium followed by return to normal Cl$^-$ medium. Since NO$^-_3$ is generally permeable through Cl$^-$ channels but, unlike Cl$^-$, does not quench SPQ changes in SPQ fluorescence intensities due to these anion substitutions measure unidirectional Cl$^-$ fluxes; the rate of change measures cell Cl$^-$ permeability. 10 μM forskolin was added subsequently to increase intracellular levels of cAMP. After a 2-min exposure to forskolin, the medium was again switched to the NO$^-_3$ medium, in the continued presence of forskolin. Thus each cell was used as its own control to evaluate the Cl$^-$ permeability induced by cAMP.

Only slow changes in SPQ fluorescence intensity were observed in cells with the frame-shift CFTR construct (as represented) by line 6B-I) upon exposure to NO$^-_3$ medium (FIG. 15A), indicating that these cells maintained a low resting Cl$^-$ permeability. Exposure of these transfected control cells to forskolin did not have any effect (n=41 cells from four passages). Similar results were obtained from cells transfected with the thymidine kinase gene only (line 2a-4A, n=22 cells) and from untransfected cells (n 18 cells).

Exposure of cells expressing CFTR to NO$^-_3$ medium similarly elicited little or no change in SPQ fluorescence intensity (as represented by line 4a-3I in FIG. 15C), indicating that CFTR expression per se did not enhance Cl$^-$ permeability. In contrast, a second exposure to NO$^-_3$, during forskolin stimulation, caused a rapid loss of intracellular Cl$^-$ (FIG. 15C). This response was highly reproducible; there was a 20- to 30-fold increase of unidirectional Cl$^-$ flux (Illsley et al, 1987) from ≈0.03 mM/s to 0.9 mM/s for each of the 10 cells in the microscopic field (FIG. 15C). Of 106 cells examined from eight passages, all responded similarly. Similar results were obtained from another cell line expressing CFTR (clone 4a-3K, n=23 cells). In the continued presence of forskolin (FIG. 15D), Cl$^-$ permeability remained enhances at near maximal levels for as long as 30 min (n=12 cells).

There were no volume changes during exposure of forskolin-stimulated CFTR cells to NO$^-_3$, indicating that the substantial changes in the intracellular concentration of Cl$^-$ were not associated with changes in cell salt content. Therefore, the Cl$^-$ fluxes were likely to be associated with equal fluxes of NO$^-_3$ in the opposite direction. The lack of changes in intracellular Cl$^-$ concentration or cell volume during forskolin stimulation in Cl$^-$ medium demonstrates that neither CFTR expression nor cAMP conferred enhanced cation conductance. Together with the enhanced Cl$^-$ permeability, cell shrinkage or swelling would have been observed if there were a high K$^+$ conductance or high Na$^+$ conductance, respectively.

Cl$^-$ permeability was also examined in cells containing a CFTRΔF508 construct. These cells (as represented by clone 5-2D, n=15 cells) exhibited low Cl$^-$ permeability under resting conditions and the permeability could not be enhanced by forskolin (FIG. 15B).

To establish that the cAMP-induced Cl$^-$ permeability in the CFTR-expressing cells was due to activation of a Cl$^-$ conductance, gramicidin was included in the normal Cl$^-$ medium to increase cation conductance of the plasma membrane. Under these conditions, the presence of Cl$^-$ channel would result in a substantial influx of both Na$^+$ and Cl$^-$, causing extensive cell swelling. Exposure to gramicidin had no effect on SPQ fluorescence or cell volume in cells with the frame-shift CFTR construct (n=13 cells) or an intact CFTR construct (n=33 cells) (FIG. 15E), supporting our conclusion (above) that resting Cl$^-$ conductance was negligible in both the control and CFTR cells. After the addition of forskolin, however, there was a marked rapid cell swelling, after a lag period of from 30 to 90 s, accompanied by elevated intracellular Cl$^-$ concentration in the cells expressing CFTR but not in control cells (FIG. 15E). These results demonstrated that the basis of cAMP-induced Cl$^-$ permeability observed in CFTR-expressing cells was a Cl$^-$ channel.

cAMP-Stimulated Cl$^-$ Currents in the CFTR-Expressing Cells

Corroborating the results of the fluorescence assay, whole-cell current was stimulated in cells expressing CFTR (FIG. 16A). After a lag period of ≈30 s, outward current in 11 of 11 cells increased dramatically to a plateau, which was sustained for 2–5 min before decreasing toward control values. This "run down" contrasts with findings using the SPQ assay, possibly reflecting a depletion of cytosolic factors necessary for sustained activation in the whole-cell patch-clamp configuration. currents evoked by the activation cocktail did not display any time-dependent voltage effects (FIG. 16B) contrast to the expressing cells, none of the 9 cells containing the frame-shift CFTR construct exhibited a response to the activation cocktail (FIG. 16A).

Current-voltage relations were essentially linear in both cell transfected with the intact CFTR and the frame-shift CFTR constructs (now shown). Slope conductances of 1.8±0.4 nS and 1.9±0.5 nS (n=9) were calculated in control cells before and after treatment with the activation mixture, respectively. The slope conductance in CFTR-expressing cells was similar (1.6±0.1 nS) but treatment with the activation mixture induced an ≈13-fold increase to 20.1±1.7 nS (n=10) (FIG. 16C).

The reversal potential of the cAMP-activated current in cells expressing CFTR was −17±5 mV, approaching the equilibrium potential for Cl$^-$ under standard conditions (E$_{Cl}$=32 mV). From this measurement, the calculated anion versus cation permeability was ≈5:1. Anion selectivity was assessed in cAMP-activated cells by replacing bath NaCl (135 mM) with sodium gluconate (135 mM). This manipulation resulted in a shift in reversal potential to +33±8 mV (n=4), toward the predicted E$_{Cl}$ of +41 mV (FIG. 16C).

The inability to construct a full-length CFTR cDNA has hampered progress in understanding the structure and function of the protein. The difficulty is mainly due to the instability of the full-length sequence in *E. coli,* where there was sequence rearrangement often associated with a short (13 bp) direct repeat in exon 6b. Through the modification of DNA sequence within the first copy of the repeat, however, we have succeeded in the construction of three different plasmids each containing the entire coding sequence. These plasmids replicate efficiently in *E. coli* (DH5α), and are intact after prolonged propagation. Although this particular modification involves the first repeat, it is understood that this second repeat can also be similarly modified instead of, or in addition to, the first repeat to achieve similar success in the propagation of the CFTR cDNA.

In addition to verification by direct DNA sequencing, the plasmids have also been examined for their ability to product proteins of expected sized in vitro and in vivo. Based on the longest open reading frame of the consensus cDNA sequence (Riordan et al 1989), a protein of 170 kd (1480 amino acids) has been predicted as the CFTR gene product. The fact that a 170 kd band was detectable in the product translated in vitro and in cells transfected with the full-length CFTR cDNA confirms the original prediction.

The availability of a full-length CFTR cDNA that can be expressed in mammalian and non-mammalian cells offers the opportunity to perform a detailed structure and function analysis of CFTR. The vectors described here are excellent tools for this purpose. With appropriate regulatory sequences inserted upstream of the coding region, it is understood that large quantities of CFTR may be produced through different kinds of heterologous gene expression systems, whereby various biochemical and biophysical studies can be performed.

The ability to express the full-length cDNA also allows development of functional assays for CFTR. In this context, Drumm et al (1990) have demonstrated through a retrovirus-intermediate that the modified full-length cDNA described here was able to confer the function of CFTR in a pancreatic carcinoma cell line (CPFAC-1) derived from a CF patient. Upon proper expression of the cDNA, the cAMP-mediated chloride transport activity was restored in this cell line, providing the first example of functional complementation of CFTR activity. The ability to confer CFTR expression in heterologous cells is an important step towards the possibility of gene therapy in the lung and pancreas of CF patients.

In order to understand the role of individual amino acid residues as well as regions of the protein, site-directed mutagenesis may be used to introduce additional mutations into the coding region of CFTR. The functional assay may also be used to confirm if the sequence alterations detected in CF patients are bona fide disease-causing mutations. The latter consideration is important if broad scale disease diagnosis and carrier screening based on DNA information are to be implemented. Further, since there is a general lack of genotypes, permanent cell lines in which the CF phenotype resists, the ability to generate heterologous cell lines capable of expressing various defective CFTR offers an alternative approach in understanding the function of CFTR and in development of rational therapy. In the latter regard, procedures can be devised for screening of compounds that would interact with the defective protein and restore its function.

To introduce additional mutations into the coding region of CFTR, it is possible to replace regions of the cDNA with altered sequences, as demonstrated by the examples described above. The procedure is difficult, however, because many of the restriction enzyme sites involved are present in more than one vector. For this reason, it is desirable to include unique restriction sites in the coding region of the cDNA. For example, by introducing a silent change (T to C) at position 1944 in exon 13, a novel BstEII site is created at the end of the sequence corresponding to the first NBF1 is probably the most interesting region in CFTR because about one-third of the disease-causing mutations reside in the region. In combination with another unique site, such as SphI, it becomes extremely easy to replace sequences for NBF1.

Finally, the full-length cDNA construct contained in the pBQ4.7 and pBW6.2 may be excised in its entirety by a single PstI digestion or a double digestion with a combination of SalI, XhoI, SmaI or EcoRV. This versatility allows the cDNA to be transferred from the current vector to other host-vector systems.

REFERENCES

Cutting, G. R., Kasch, L. M., Rosenstein, B. J., Zielenski, J., Tsui, L.-C., Antonarakis., S. E. and Kazazian, H. H. Jr. (1990) "A Cluster of Cystic Fibrosis Mutations in the First Nucleotide-Binding Fold of the Cystic Fibrosis Conductance Regulator Protein" *Nature* 346:366–369.

Drumm, M. L., Pope, H. A., Cliff, W. H., Rommens, J. M., Marvin, S. A., Tsui, L.-C., Collins, F. S., Frizzel, R. A. and Wilson, J. M. (1990) "Correction of the Cystic Fibrosis Defect in vitro by Retrovirus-Mediated Gene Transfer" *Cell* 62:1227–1233

Hawley, D. K. and McClure, W. R., (1983) *Nucleic Acids Res.* 11:2237–2255

Higuchi, R., Krummel, B., and Saiki, R. K., (1988) "A General Method of in vitro Preparation and Specific Mutagenesis of DNA Fragments: Study of Protein and DNA Interactions", *Nucleic Acids Res.* 16:7351–7363.

Ho, S. N., Hunt, H. D., Horton, R. M., Pullen, J. K., and Pease, L. R. (1989) "Site-Directed Mutagenesis by Overlap Extension Using the Polymerase Chain Reaction", *Gene* 77:51–59.

Kerem, B., Rommens, J. M., Buchanan, J. A., Markiewicz, D., Cox, T. K., Chakravarti, A., Buchwald, M. and Tsui, L.-C., (1989) "Identification of the Cystic Fibrosis Gene: Genetic Analysis" *Science* 245:1073–1080.

Laemmli, U. K., (1970) *Nature* 227:680–685.

Meakin, S. O., Du, R. P., Tsui, L.-C. and Breitman, M. L. (1987) "γ-Crystallins of the Human Eye Lens: Expression Analysis of Five Members of the Gene Family", *Molec. Cell. Biol.* 7:2671–2679.

Riordan, J. R., Rommens, J. M., Kerem, B., Alon, N., Rozmahel, R., Grzelchak, K., Zielenski, J., Lok, S., Plavsic, N., Chou J.-L., Drumm, M. L., Iannuzzi, M. C., Collins, F. S., and Tsui, L.-C., (1989) "Identification of the Cystic Fibrosis Gene: Cloning and Characterization of Complementary DNA", *Science* 245:1055–1073.

Rommens, J. M., Iannuzzi, M. C., Kerem, B., Melmer, G., Drumm, M. L., Melmer, G., Dean, M., Rozmahel, R., Cole J. L., Kennedy, D., Hidaka, N., Zsiga, M., Buchwald, M., Riordan, J. R., Tsui, L.-C., and Collins, F. S., (1989). "Identification of the Cystic Fibrosis Gene: Chromosome Walking and Jumping" *Science* 245:1059–1065

Saiki, R., Sambrook, J., Fritsch, E. F. and Maniatis, T., (1989) *Molecular Cloning* Second Edition, Cold Spring Harbor Laboratory Press, NY.

Twobin, H., Staehelin, T. and Gordon J., (1979) *Proc. Natl. Acad. Sci USA* 76:4350–4354.

Boat, T., Welsh, M. J. & Beaudet, A. (1989) in *The Metabolic Basis of Inherited Disease,* eds. Scriver, C. R., Beaudet, A. L., Sly. W. S. & Valle, D. (McGraw, Hill, New York), 6th Ed., pp. 2649–2680.

Rommens, J. M., Ianuzzi, M. C., Kerem, B., Drumm, M. L., Melmer, G., Dean, M., Rozmahel, R., Cole, J. L., Kennedy, D., Hidaka, N., Zsiga, M., Burchwald, M., Riordan, J. R., Tsui, L.-C. & Collins. F. S. (1989) *Science* 245, 1059–1065.

Riordan, J. R., Rommens, J. M., Kerem, B., Alon, N., Rozmahel, R., Grzelczack, Z., Zielenski, J., Lok, S., Plavsic, N., Chou, J.-L., Drumm, M. L., Iannuzzi, M. C., Collins, Tsui, L.-C. (1989) *Science* 245, 1066–1072.

Kerem, B., Riommens, J. M., Buchanan, J. A., Markiewicz, D., Cox, T. K., Chakravarti, A., Buchwald, M. & Tsui, L.-C. (1989) *Science* 245, 1073–1080).

Dean, M., White, M. B., Amos, J., Gerrard, B, Stewart, C., Khaw, K.-T., & Leppert, M. (1990) *Cell* 61, 863–870.

Cutting, G. R., Kasch, L. M., Rosenstein, B. J., Zielenski, J., Tsui, L.-C., Kazazian, H. H., Jr., & Antonarakas, S. E. (1990) *Nature (London)* 346, 366–369.

Kerem, B., Zielenski, J., Markiewicz, D., Bozon, D., Gazit, E., Yahav, J., Kennedy, D., Riordan, J. R., Collins, F. S., Rommens, J. M. & Tsui, L.-C. (1990) *Proc. Natl. Acad. Sci.* 87, 8447–8451.

White, M. B., Amos, J., Hsu, J. M. C., Gerrard, B., Finn, P. & Dean, M. (1990) *Nature (London)* 344, 665–667.

Zielenski, J., Bozon, D., Kerem, B., Markiewicz, D., Durie, P., Rommens, J. M. & Tsui, L.-C. (1991) *Genomics* 10, 229–235.

Hyde, S. C., Emsley, P., Hartshorn, M. J., Mimmack, M. M., Gileadi, U., Pearce, S. R., Gallagher, M. P., Gill, D. R., Hubbard, R. E. & Higgins, C. F. (1990) *Nature (London)* 346, 362–365.

Gregory, R. J., Cheng, S. H., Rich, D. P., Marshall, J., Paul, S., Hehir, K., Ostedgaard, L., Klinger, K. W., Welsh, M. J. & Smith, A. E. (1990) *Nature (London)* 347, 382–386.

Drumm, M. L., Pope, H. A., Clift, W. H., Rommens, J. M., Marvin, S. A., Tsui, L.-C., Collins, F. S., Frizzell, R. & Wilson, J. M. (1990) *Cell* 62, 1227–1233.

Rich, D. P., Anderson, M. P., Gregory, R. J., Cheng, S. H., Paul, S., Jefferson, D. M., McCann, J. D., Klinger, K. W., Smith, A. E. & Welsh, M. J. (1990) *Nature (London)* 347, 358–363.

Kartner, N., Jensen, T. J., Naismith, A. L., Sun, S., Ackerley, C. A., Reyes, E. F., Tsui, L.-C., Rommens, J. M., Bear, C. E., & Riordan, J. R. (1991) *Cell*.

Anderson, M. P., Rich, D. P., Gregrory, R. J., Smith, A. E., Welsh, M. J. (1991) *Science* 251, 679–682.

Meakin, S. O., Du, R. P., Tsui, L.-C. & Breitman, M. L. (1987) *Mol. Cell. Biol.* 7, 2671–2679.

Karin, M. & Richards, R. I. (1982) *Nature (London)* 299, 797–802.

Sambrook, J., Fritsch, E. F. & Maniatis, T. (1989) *Molecular Cloning: A Laboratory Manual* (Cold Spring Harbor Lab., Cold Spring Harbor, N.Y.), 2nd Ed.

Higuchi, R., Krummel, B. & Saiki, R. K. (1988) *Nucleic Acids Res.* 16, 7351–7363.

Ho, S. N., Hunt, H. D., Horton, R. M., Pullen, J. K. & Pease, L. R. (1989) *Gene* 77, 51–59.

Miller, S. A., Dykes, D. D. & Polesky, H. F. (1988) *Nucleic Acids Res.* 16, 1215.

MacDonald, R. J., Swift, G. H., Przbyla, A. E. & Chirgwin, J. M. (1987) *Methods Enzymol.* 152, 219–227.

Laemmli, U.K. (1970) *Nature (London)* 227, 680–685.

Towbin, H., Staehelin, T. & Gordon, J. (1979) *Proc. Natl. Acad. Sci. USA* 76, 4350–4354.

Forskett, J. K. (1988) *Am. J. Physiol.* 255, C566–C571.

Forskett, J. K. & Melvin, J. E. (1989) *Science* 244, 1582–1585.

Forskett, J. K. (1990) *Am. J. Physiol.* 259, C998–C1004.

Hamill, O. P., Marty, A., Neher, E., Sakmann, B. & Sigworth, F. J. (1981) *Pfügers Arch.* 391, 85–100.

Cheng, S. H., Gregory, R. J., Marshall, J., Paul, S., Souza, D. W., White, G. A., O'Riordan, C. R. & Smith, S. E. (1990) Cell 63, 827–834.

Illsley, N. P. & Verkman, A. S. (1987) *Biochemistry* 26, 1215–1219.

Cliff, W. H. & Frizell, R. A. (1990) *Proc. Natl Acad. Sci. USA* 87, 4956–4960.

Tabcharani, J. A., Low, W., Elie, D. & Hanrahan, J. W. (1990) *FEBS Lett.* 270, 157–164.

Gray, M. A., Pollard, C. E., Harris, A., Coleman, L., Greenwell, J. R. & Argent, B. E. (1990) *Am. J. Physiol.* 259, C752–C761.

Ringe, D. & Petsko, G. A. (1990) *Nature (London)* 346, 312–313.

---

We claim:

1. A variant DNA sequence encoding a cystic fibrosis transmembrane conductance regulator (CFTR) protein, said gene having at least 27 exons which form the normal cDNA which codes for CFTR protein, said normal cDNA including exons 6a and 6b wherein exon 6b includes a 13 bp repeat, said variant DNA sequence comprising at least one of said 13 bp repeats of exon 6b having one or more nucleotide substitutions in said 13 bp repeat wherein the amino acid sequence of the protein encoded by said DNA sequence is not changed by said one or more substitutions.

2. The variant cDNA sequence of claim 1 wherein said one or more nucleotide substitutions are at positions 930 and/or 933 and said substitutions are C for T at 930 and G for A at 933.

3. The variant cDNA sequence of claim 1 further comprising a nucleotide substitution at position 936, said substitution being C for T.

* * * * *

UNITED STATES PATENT AND TRADEMARK OFFICE
CERTIFICATE OF CORRECTION

PATENT NO.   : 6,063,913
DATED        : May 16, 2000
INVENTOR(S)  : Tsui et al.

It is certified that error appears in the above-identified patent and that said Letters Patent is hereby corrected as shown below:

Title page,
Item [54], line 2, in the title, "CDNA" should read -- cDNA --.

Item [56], References Cited, OTHER PUBLICATIONS,
Line 6, "2671-267" should read -- 2671-2679 --;
Line 7, "expresion" should read -- expression --;

Item [56], page 2, column 1,
Line 13 - 14, "Adenocarinom" should read -- Adenocarcinoma --
Line 56, "107(106)" should read --107(6) --.

Column 1,
Line 2: in the title, "CDNA" should read -- cDNA --.

Signed and Sealed this

Eleventh Day of September, 2001

Attest:

Nicholas P. Godici

NICHOLAS P. GODICI
*Attesting Officer*      *Acting Director of the United States Patent and Trademark Office*